United States Patent
Kato et al.

(10) Patent No.: US 9,268,145 B2
(45) Date of Patent: Feb. 23, 2016

(54) IMAGE DISPLAY SYSTEM AND THREE-DIMENSIONAL EYEGLASSES

(71) Applicant: Panasonic Intellectual Property Management Co., Ltd., Osaka (JP)

(72) Inventors: Yumiko Kato, Osaka (JP); Jun Ozawa, Nara (JP); Tsuyoshi Inoue, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 218 days.

(21) Appl. No.: 13/865,684

(22) Filed: Apr. 18, 2013

(65) Prior Publication Data

US 2013/0229711 A1 Sep. 5, 2013

Related U.S. Application Data

(63) Continuation of application No. PCT/JP2012/002910, filed on Apr. 27, 2012.

(30) Foreign Application Priority Data

May 19, 2011 (JP) ................................. 2011-112198

(51) Int. Cl.
*G02B 27/22* (2006.01)
*H04N 13/04* (2006.01)
*A61B 5/16* (2006.01)

(52) U.S. Cl.
CPC . *G02B 27/22* (2013.01); *A61B 5/16* (2013.01); *H04N 13/0438* (2013.01); *H04N 13/0497* (2013.01); *H04N 2213/002* (2013.01); *H04N 2213/008* (2013.01)

(58) Field of Classification Search
CPC .......... H04N 13/0438; H04N 13/0497; H04N 2213/002; H04N 2213/008; G02B 27/2264; G02B 27/2214; G02B 27/26; A61B 5/16

USPC .............. 359/464–466, 458, 473; 348/53, 56; 463/40, 42
See application file for complete search history.

(56) References Cited

U.S. PATENT DOCUMENTS

| 5,522,041 A | 5/1996 | Murakami et al. |
|---|---|---|
| 5,821,989 A * | 10/1998 | Lazzaro et al. ................. 348/56 |

(Continued)

FOREIGN PATENT DOCUMENTS

| JP | 6-326856 | 11/1994 |
|---|---|---|
| JP | 8-204703 | 8/1996 |
| JP | 2004-248106 | 9/2004 |
| JP | 2006-305325 | 11/2006 |
| JP | 2007-319187 | 12/2007 |

(Continued)

OTHER PUBLICATIONS

International Search Report issued Jul. 24, 2012 in corresponding International Application No. PCT/JP2012/002910.

*Primary Examiner* — Scott J Sugarman
*Assistant Examiner* — Mustak Choudhury
(74) *Attorney, Agent, or Firm* — Wenderoth, Lind & Ponack, L.L.P.

(57) ABSTRACT

Provided is an image display system which can assuredly perform collaborative processing such as determination of a fatigue state of a viewer using three-dimensional eyeglasses and an image display apparatus, without increasing system scale, the image display system including: a transmitting and receiving unit included in a three-dimensional display TV which transmits to three-dimensional eyeglasses a specification-designating signal designating a specification which at least includes a data format for a communication signal; a transmitting and receiving unit included in the three-dimensional eyeglasses which receives the specification-designating signal transmitted from the three-dimensional display TV and, according to the specification designated by the received specification-designating signal, converts a biometric signal acquired by a biometric signal sensor into the communication signal, and transmits the communication signal to the three-dimensional display TV.

20 Claims, 26 Drawing Sheets

(56) References Cited

U.S. PATENT DOCUMENTS

| | | | |
|---|---|---|---|
| 5,835,789 A | 11/1998 | Ueda et al. | |
| 6,508,709 B1* | 1/2003 | Karmarkar | 463/42 |
| 7,027,621 B1* | 4/2006 | Prokoski | 382/118 |
| 2009/0099785 A1 | 4/2009 | Yamamoto et al. | |
| 2010/0157425 A1 | 6/2010 | Oh | |
| 2010/0228139 A1 | 9/2010 | Nanba et al. | |
| 2010/0309535 A1 | 12/2010 | Landowski et al. | |
| 2011/0028805 A1 | 2/2011 | Yamazaki | |
| 2011/0216175 A1* | 9/2011 | Shimoyama et al. | 348/56 |

FOREIGN PATENT DOCUMENTS

| | | |
|---|---|---|
| JP | 2008-109527 | 5/2008 |
| JP | 2009-93509 | 4/2009 |
| JP | 2010-154533 | 7/2010 |
| JP | 2010-207347 | 9/2010 |
| JP | 2011-28633 | 2/2011 |
| JP | 2011-188118 | 9/2011 |
| WO | 2010/143455 | 12/2010 |
| WO | 2010/144478 | 12/2010 |

* cited by examiner

| Data transmission specification ID | Data transmission specification ||||
|---|---|---|---|---|
| | Utilized biometric information ID | Data level ID | Transmission frequency | Data structure |
| 001 | 001 | 001 | 1/120s | Sampling frequency: 2 bytes<br>Data accuracy: 2 bytes<br>Time length: 2 bytes<br>Utilized electrode number: 2 bytes<br>Electrode 1: 24000 bytes<br>Electrode 2: 24000 bytes<br>Electrode 3: 24000 bytes<br>Electrode 4: 24000 bytes<br>Electrode 5: 24000 bytes |
| 002 | 002 | 002 | 1/120s | Time length: 2 bytes<br>Data accuracy: 2 bytes<br>Amount of movement: 2 bytes |
| 003 | 007 | 001 | 1/300s | Sampling frequency: 2 bytes<br>Data accuracy: 1 byte<br>Time length: 2 bytes<br>Utilized electrode number: 2 bytes<br>Electrode 1: 15000 bytes<br>Electrode 2: 15000 bytes |
| 004 | 007 | 003 | 1/300s | Level of fatigue: 1 byte |

Utilized biometric information:
 001 = Speed of convergence and divergence movements
 002 = Amounts of convergence and divergence movements
 003 = Amount of involuntary eye movements
 004 = Change in speed of saccade
 005 = Saccade distance at a time
 006 = Saccade rate per fixed time period
 007 = Blink rate per fixed time period Data level: 001 = Raw sensor output
 002 = Data processed by signal processing such as filtering
 003 = Determination result of viewer state

FIG. 5

| Indicator for use in fatigue detection, extractable from electrooculogram | Both eyes/one eye (number of electrodes) | Sampling frequency | Number of bits (amplitude resolution) | Unit time (transmission time intervals) |
|---|---|---|---|---|
| Change in convergence and divergence movements to the same target | Both eyes (6) | 200 Hz or greater | 16 bits or greater | 5 seconds to content dependent |
| Change in speed of convergence and divergence movements (mean and variance per unit time) | Both eyes (6) | 200 Hz or greater | 16 bits or greater | to 5 minutes |
| Amounts of convergence and divergence movements (grand total in viewing time) | Both eyes (6) | 100 Hz or greater | 16 bits or greater | 1 to 10 minutes |
| Amount of involuntary eye movements (grand total in time, mean per unit time) | One eye (5) | 500 Hz or greater | 16 bits or greater | to 1 minute |
| Change in speed of saccade (mean and variance per unit time) | One eye (5) | 200 Hz or greater | 16 bits or greater | 5 seconds to 5 minutes |
| Saccade distance at a time (mean per unit time) | One eye (5) | 100 Hz or greater | 16 bits or greater | 5 seconds to 5 minutes |
| Saccade rate per fixed time period | One eye (3) | 50 Hz or greater | 8 bits or greater | 1 to 10 minutes |
| Blink rate per fixed time period | One eye (3) | 50 Hz or greater | 4 bits or greater | 5 to 15 minutes |

| Indicator for use in fatigue detection, extractable from electrooculogram | Unit time | Measurement data amount per unit time | Intermediate processing content | Amount of intermediate processing result data per unit time |
|---|---|---|---|---|
| Change in convergence and divergence movements to the same target | 1 minute | 120000 bytes | BPF, antiphase movement extraction | 48000 bytes |
| Change in speed of convergence and divergence movements (mean and variance per unit time) | 1 minute | 120000 bytes | BPF, antiphase movement extraction | 48000 bytes |
| Amounts of convergence and divergence movements (grand total in time) | 5 minutes | 300000 bytes | BPF, antiphase movement extraction, $\Sigma \mid \Delta t \mid$ | 2 bytes |
| Amount of involuntary eye movements (grand total in time, mean per unit time) | 30 seconds | 90000 bytes | BPF, $\Sigma \mid \Delta t \mid$ | 2 bytes |
| Change in speed of saccade (mean and variance per unit time) | 1 minute | 72000 bytes | BPF, differential amplification | 14000 bytes |
| Saccade distance at a time (mean per unit time) | 1 minute | 38000 bytes | BPF | |
| Saccade rate per fixed time period | 5 minutes | 90000 bytes | BPF, saccade extraction | 2 bytes |
| Blink rate per fixed time period | 10 minutes | 75000 bytes | Thresholding, blinking extraction | 2 bytes |

FIG. 11A

| Data transmission specification ID | Utilized biometric information | Data transmission specification | | Corresponding eyeglasses ID |
| --- | --- | --- | --- | --- |
| | | Data level | Data structure | |
| 001 | Change in speed of convergence and divergence movements | Sensor output | Sampling frequency: 2 bytes<br>Data accuracy: 2 bytes<br>Time length: 2 bytes<br>Electrode 1: 24000 bytes<br>Electrode 2: 24000 bytes<br>Electrode 3: 24000 bytes<br>Electrode 4: 24000 bytes<br>Electrode 5: 24000 bytes | P12-34<br>P12-35<br>P12-36<br>S08-21<br>S08-22<br>S08-41<br>... |
| 002 | Amounts of convergence and divergence movements | Intermediate output | Time length: 2 bytes<br>Data accuracy: 2 bytes<br>Amount of movement: 2 bytes | P13-34<br>P13-35<br>P15-36<br>S09-11<br>... |

163

```
<xml="xxxxxx.dtd">
<head>
  <from_display_id>tv314</from_display_id>
  <to_glass_id>P12-34<to_glass_id>
</head>
<body>
  <transfer_data_format_byte>
    <data_frequency>2</data_frequency>
    <data_acuracy>2</data_acuracy>
    <data_time>2</data_time>
    <item_term_num ="5">24000</item_term_num>
</transfer_data_format_byte>
</body>
```

| Integrated amount of convergence and divergence movements (μV) | Fatigue indicator |
|---|---|
| to 2000 | 1 |
| to 7000 | 2 |
| to 11000 | 3 |
| to 14000 | 4 |
| to 16000 | 5 |
| to 17000 | 6 |
| to 17500 | 7 |
| to 17900 | 8 |
| to 18200 | 9 |
| to 18400 | 10 |

FIG. 16

(Example A)

Eyeglasses ID: P12-34
  Transmission specification: Sampling frequency = 2 bytes
                              Data accuracy = 2 bytes
                              Time length = 2 bytes
                              Electrode 1 = 24000 bytes
                              Electrode 2 = 24000 bytes
                              Electrode 3 = 24000 bytes
                              Electrode 4 = 24000 bytes
                              Electrode 5 = 24000 bytes (Example B)

Eyeglasses ID: P15-00
  Transmission specification 1: Sampling frequency = 2 bytes
                                Data accuracy = 2 bytes
                                Time length = 2 bytes
                                Electrode 1 = 24000 bytes
                                Electrode 2 = 24000 bytes
                                Electrode 3 = 24000 bytes
                                Electrode 4 = 24000 bytes
                                Electrode 5 = 24000 bytes
  Transmission specification 2: Time length = 2 bytes
                                Data accuracy = 2 bytes
                                Amounts of convergence movements
                                = 2 bytes

FIG. 17

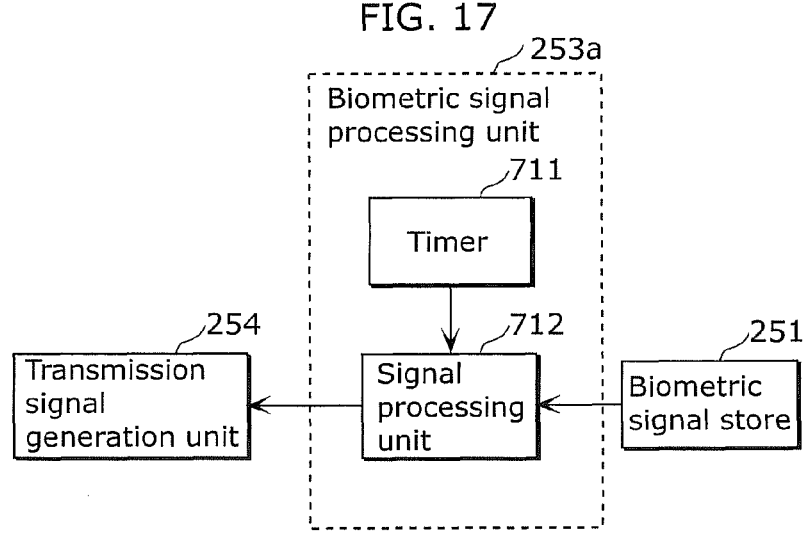

FIG. 25

| Blink rate (count) | Fatigue indicator |
|---|---|
| 37 and more | 1 |
| to 36 | 2 |
| to 34 | 3 |
| to 32 | 4 |
| to 30 | 5 |
| to 27 | 6 |
| to 24 | 7 |
| to 20 | 8 |
| to 15 | 9 |
| to 10 | 10 |

734

(a) Example of communication format (b) Example of XML structured format

```
<xml="xxxxxx.dtd">
<head>
  <glass_id>P21<glass_id>
  <glass_version>0062</glass_version>
  <glass_open>1</glass_open>
</head>
<body>
  <fatigu_grade="3"/>
</body>
```

IMAGE DISPLAY SYSTEM AND THREE-DIMENSIONAL EYEGLASSES

CROSS REFERENCE TO RELATED APPLICATIONS

This is a continuation application of PCT Patent Application No. PCT/JP2012/002910 filed on Apr. 27, 2012, designating the United States of America, which is based on and claims priority of Japanese Patent Application No. 2011-112198 filed on May 19, 2011. The entire disclosures of the above-identified applications, including the specifications, drawings and claims are incorporated herein by reference in their entirety.

FIELD

One or more exemplary embodiments disclosed herein relate generally to an image display system which includes three-dimensional eyeglasses and an image display apparatus which presents a three-dimensional image to a viewer.

BACKGROUND

Three-dimensional videos are becoming popular not only as large screen movies but also as TV content and game footage with the growing popularity of household three-dimensional TVs and computer displays. A three-dimensional video gives a viewer illusion as if the video has depth by creating a disparity between respective images presented to the right and left eyes. Unlike the conventional two-dimensional videos, when viewing a three-dimensional video, the right eye and the left eye move along with the depth of a subject. In other words, when the depth is small and the subject appears projected forward, the left and right eyes move in a direction in which the viewer goes cross-eyed, when the depth is great and the subject appears at far distance, a state of the eyes is close to a state in which the eyes look straight ahead. On the other hand, because the position of a display remains fixed, the viewer is required to continuously be focused at the position of the display for clear viewing. Thus, the focal length of the video is fixed to the position of the display. Due to such conflict between the focal length and the eye movement to the virtual depth of the subject, it is conceived that physical symptoms such as fatigue and video-induced motion sickness may appear in the viewer involved with viewing a stereoscopic video. Thus, conventionally, the viewer fatigue is determined, in PTL 1, by measuring the optical characteristics of the viewer's eyes viewing the three-dimensional video.

On the other hand, to present different images to the left and right eyes using one display, it is necessary to use dedicated eyeglasses (Hereinafter, also referred to as "three-dimensional eyeglasses.") and use shutters to select light directed to the left and right eyes. Switching the shutters in synchronization with right-eye and left-eye screen displays at a sufficiently high frequency allows the viewer to perceive a stereoscopic view, fusing information to the eyes without noticing that the right-eye and left-eye images are being switching.

Meanwhile, during the display of the three-dimensional video, when a viewer sees the display without wearing the dedicated eyeglasses, the viewer not only cannot perceive the stereoscopic view but also sees double imaging. Thus, in PTL 2, to assuredly achieve a stereoscopic view, whether a viewer is wearing the dedicated eyeglasses is sensed in contact or non-contact with the dedicated eyeglasses, and the dedicated eyeglasses transmit a signal indicative of the wearing conditions to a display device which controls video display, such as TV, computers, and game consoles. This controls the switching of the two-dimensional video display and the three-dimensional video display in the display device.

CITATION LIST

Patent Literature

[PTL 1] Japanese Unexamined Patent Application Publication No. 2006-305325
[PTL 2] Japanese Unexamined Patent Application Publication No. 2010-154533

SUMMARY

Technical Problem

In the method disclosed in PTL 1, however, for detection of the fatigue state, a large instrument including an lens array is installed and the optical characteristics of the viewer's eyes is measured where positions of the viewer's eyes are fixed, which is inconvenient for the viewer to enjoy a three-dimensional video independent of the position and the posture. Many of biometric signals which include eye condition to determine the viewer state such as fatigue among other things are analyzed by a specific method depending on the type of the signal as seen in PTL 1. Thus, if the dedicated eyeglasses are not compatible with an analysis method for biometric signals of a display device such as TV which controls video display, there is a problem that it is difficult to determine a viewer state while dedicated eyeglasses are used to sense whether the viewer is wearing the eyeglasses as described in PTL 2.

Thus, one non-limiting and exemplary embodiment provides the image display system and the three-dimensional eyeglasses which can assuredly perform collaborative processing such as determination of the fatigue state of the viewer using the three-dimensional eyeglasses and the image display apparatus, without increasing system scale.

Solution to Problem

In one general aspect, the techniques disclosed here feature an image display system for presenting a three-dimensional image to a viewer, the image display system including: an image display apparatus for alternately outputting a left-eye image and a right-eye image to be presented to a left eye and a right eye, respectively, of a viewer; and three-dimensional eyeglasses having a left-eye shutter and a right-eye shutter for being worn by the viewer over face or head and setting the left-eye shutter to an open state when the left-eye image is displayed by the image display apparatus and setting the right-eye shutter to the open state when the right-eye image is displayed by the image display apparatus, wherein the three-dimensional eyeglasses include: a biometric signal measurement unit configured to measure a physical state of the viewer to acquire a biometric signal; and a transmitting and receiving unit configured to convert the biometric signal acquired by the biometric signal measurement unit into a communication signal and transmit the communication signal to the image display apparatus, wherein the image display apparatus includes a transmitting and receiving unit configured to receive the communication signal transmitted from the three-dimensional eyeglasses, and the transmitting and receiving unit included in the image display apparatus is configured to transmit, to the three-dimensional eyeglasses, a specification-designating signal designating a specification including at least a data format for the communication signal, and the transmitting and receiving unit included in the three-dimensional eyeglasses is configured to receive the specification-designating signal transmitted from the image display apparatus, convert the biometric signal into the communication signal, according to the specification designated by the received specification-designating signal, and transmit the communication signal to the image display apparatus.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

The image display system and the three-dimensional eyeglasses according to one or more exemplary embodiments or features disclosed herein can be provided which can assuredly perform collaborative processing such as determination of the fatigue state of the viewer using the three-dimensional eyeglasses and the image display apparatus, without increasing system scale.

Thus, the image display system and the three-dimensional eyeglasses according to one or more exemplary embodiments have significant practical value for its application today where the opportunity of viewing three-dimensional videos at households are increasing.

BRIEF DESCRIPTION OF DRAWINGS

These and other advantages and features will become apparent from the following description thereof taken in conjunction with the accompanying Drawings, by way of non-limiting examples of embodiments of the present disclosure.

In the Drawings:

FIG. 4 is a diagram showing an example of indicator specification information (transmission specification) stored in a transmission specification store.

FIG. 5 is a diagram showing a list indicative of acquisition conditions of biometric information available for specifying fatigue from electrooculogram (top), and a list indicative of unit time and amounts of data per unit time prior to processing and after intermediate processing (bottom).

FIG. 11A is a diagram showing an example of measurement specifications stored in a measurement specification store according to the embodiment.

FIG. 16 is a diagram showing an example of transmission specifications stored in the transmission specification store according to the embodiment.

FIG. 17 is a block diagram showing an example of the detailed configuration of a biometric signal processing unit according to the embodiment.

FIG. 25 is a diagram showing an example of data stored in a blink rate-fatigue correspondence table according to the embodiment.

Figure 1:
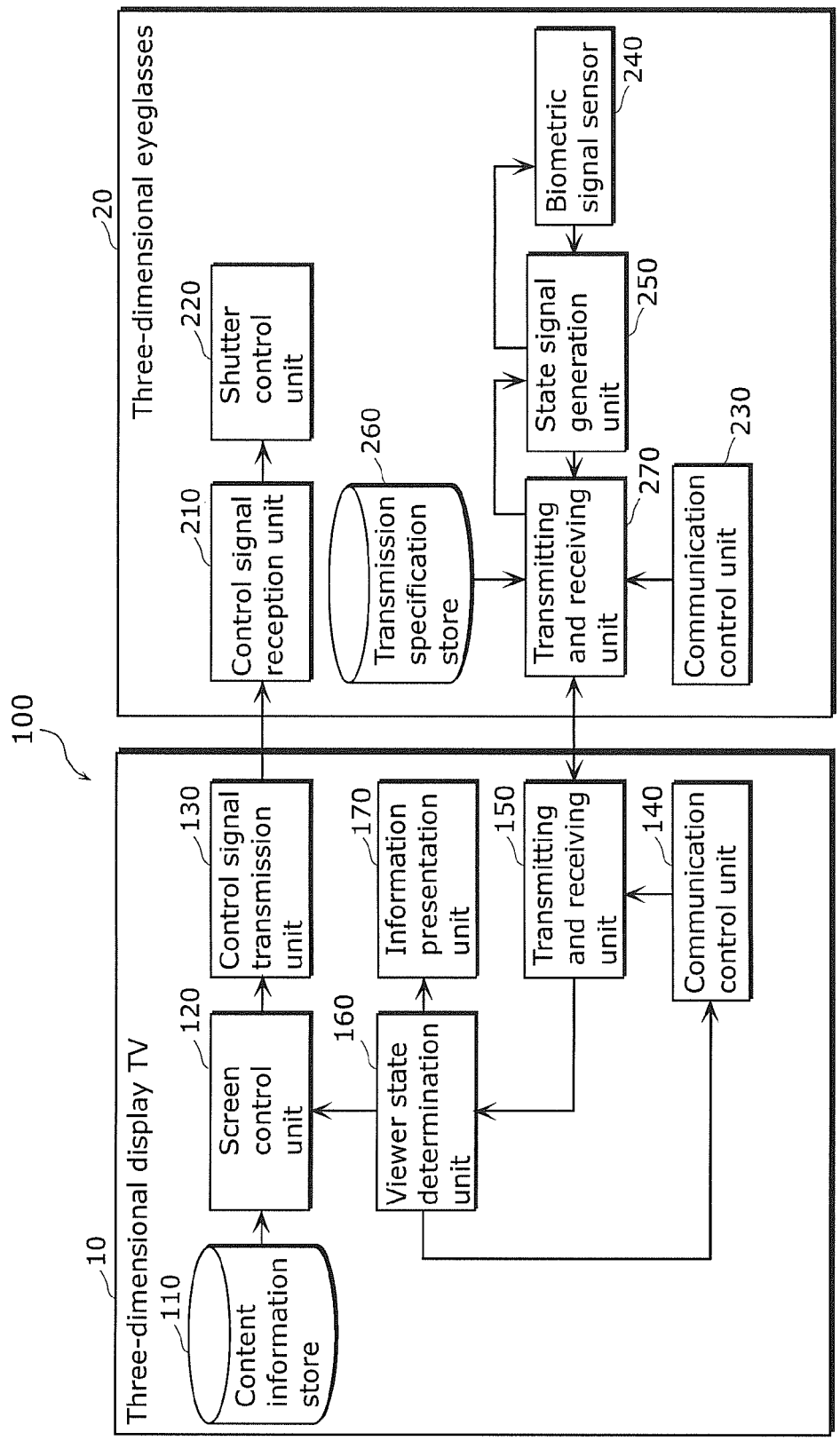
FIG. 1 is a block diagram showing an example configuration of an image display system according to an exemplary embodiment.

DESCRIPTION OF EMBODIMENT (Overview of Present Invention)

An image display system according an exemplary embodiment disclosed herein is an image display system for presenting a three-dimensional image to a viewer, the image display system including: an image display apparatus for alternately outputting a left-eye image and a right-eye image to be presented to a left eye and a right eye, respectively, of a viewer; and three-dimensional eyeglasses having a left-eye shutter and a right-eye shutter for being worn by the viewer over face or head and setting the left-eye shutter to an open state when the left-eye image is displayed by the image display apparatus and setting the right-eye shutter to the open state when the right-eye image is displayed by the image display apparatus, wherein the three-dimensional eyeglasses include: a biometric signal measurement unit configured to measure a physical state of the viewer to acquire a biometric signal; and a transmitting and receiving unit configured to convert the biometric signal acquired by the biometric signal measurement unit into a communication signal and transmit the communication signal to the image display apparatus, wherein the image display apparatus includes a transmitting and receiving unit configured to receive the communication signal transmitted from the three-dimensional eyeglasses, and the transmitting and receiving unit included in the image display apparatus is configured to transmit, to the three-dimensional eyeglasses, a specification-designating signal designating a specification including at least a data format for the communication signal, and the transmitting and receiving unit included in the three-dimensional eyeglasses is configured to receive the specification-designating signal transmitted from the image display apparatus, convert the biometric signal into the communication signal, according to the specification designated by the received specification-designating signal, and transmit the communication signal to the image display apparatus.

According to the above configuration, the three-dimensional eyeglasses convert the biometric signal acquired by the biometric signal measurement unit included in the three-dimensional eyeglasses into the communication signal, according to a specification designated by the specification-designating signal transmitted from the image display apparatus, and transmits the communication signal to the image display apparatus. In other words, the image display apparatus and the three-dimensional eyeglasses reconcile a communication format such as a data format of the biometric signal to be transmitted from the three-dimensional eyeglasses to the image display apparatus. Thus, in any combination of the image display apparatus and the three-dimensional eyeglasses, for example, a combination of the image display apparatus and the three-dimensional eyeglasses that are made by different manufacturers and/or at different times of manufacturing, biometric information of the viewer is transmitted from the three-dimensional eyeglasses to the image display apparatus in a communication specification, such as a data format, in which the image display apparatus can receive the biometric information. Thus, the image display apparatus can perform various processing (such as determining a level of fatigue) based on the biometric information on the viewer.

For example, a state of image display in the image display apparatus is changed based on the physical state of the viewer in the middle of viewing the three-dimensional image, thereby allowing for more comfortable three-dimensional image viewing, switching to a two-dimensional image, prevention of problems due to fatigue or video-induced motion sickness, processing such as restriction of viewing images.

Thus, the image display system can be implemented which can assuredly perform collaborative processing such as determination of the fatigue state of the viewer using the three-dimensional eyeglasses and the image display apparatus, without increasing system scale.

Herein, the three-dimensional eyeglasses may further include a transmission specification store storing at least one transmission specification which is information indicative of a specification in which the three-dimensional eyeglasses can transmit the communication signal to the image display apparatus, the transmitting and receiving unit included in the three-dimensional eyeglasses may further transmit the at least one transmission specification stored in the transmission specification store to the image display apparatus, and the transmitting and receiving unit included in the image display apparatus may receive the at least one transmission specification transmitted from the three-dimensional eyeglasses, and transmit to the three-dimensional eyeglasses, as the specification-designating signal, a signal indicative of at least one transmission specification selected from among the received at least one transmission specification.

More specifically, the image display apparatus may further include: a measurement specification store storing at least one measurement specification which is information indicative of a specification in which the transmitting and receiving unit included in the image display apparatus can receive the communication signal; and a measurement specification determination unit configured to determine a measurement specification for use in determining the physical state of the viewer, from among the at least one measurement specification stored in the measurement specification store, wherein the transmitting and receiving unit included in the image display apparatus may transmit to the three-dimensional eyeglasses, as the specification-designating signal, a signal indicative of a transmission specification corresponding to the measurement specification determined by the measurement specification determination unit, among the at least one transmission specification transmitted from the three-dimensional eyeglasses.

According to the above configuration, first, the three-dimensional eyeglasses transmit, to the image display apparatus, the transmission specifications that may be employed by the three-dimensional eyeglasses, and the image display apparatus that has received the transmission specifications selects a transmission specification (a transmission specification corresponding to the measurement specification) in which the image display apparatus can receive data, from among the received transmission specifications and transmits a specification-designating signal indicative of the selection result to the three-dimensional eyeglasses. Thus, the biometric signal is more assuredly transmitted from the three-dimensional eyeglasses to the image display apparatus in a data format that can be handled by both the three-dimensional eyeglasses and the image display apparatus.

In other words, even when the image display apparatus and the three-dimensional eyeglasses are not manufactured by the same manufacturer or have the same model, or are not devices dedicated to each other, the image display apparatus can reconcile the transmission specification in which the image display apparatus can receive the biometric signal and the transmission specification in which the three-dimensional eyeglasses can transmit data.

Moreover, the transmitting and receiving unit included in the three-dimensional eyeglasses may transmit an eyeglasses ID, which is a signal identifying the three-dimensional eyeglasses, to the image display apparatus, the transmitting and receiving unit included in the image display apparatus may receive the eyeglasses ID transmitted from the three-dimensional eyeglasses, and the measurement specification determination unit may determine whether a measurement specification corresponding to the received eyeglasses ID is stored in the measurement specification store and, determine the measurement specification as the one measurement specification when the measurement specification is stored in the measurement specification store, and request the three-dimensional eyeglasses to transmit a transmission specification stored in the transmission specification store to the image display apparatus when the measurement specification is not stored in the measurement specification store.

According to the above configuration, when the eyeglasses ID is associated with the transmission specification of the biometric information which is transmitted from the three-dimensional eyeglasses to the image display apparatus, by simply receiving the eyeglasses ID, the image display apparatus can know the transmission specification that may be employed by the three-dimensional eyeglasses. Thus, the image display apparatus can obtain the transmission specification of the three-dimensional eyeglasses using less communications, without being required to transmit redundant transmission specifications to the three-dimensional eyeglasses. In particular, if there are multiple transmission specifications that may be employed by the three-dimensional eyeglasses, transmission of one data item (the eyeglasses ID) from the three-dimensional eyeglasses, irrespective of the number of the transmission specifications, allows the image display apparatus to acquire (i.e., recognize) all the transmission specifications of the three-dimensional eyeglasses.

Moreover, the transmission specification or the specification-designating signal may include an array of plural signals indicative of the physical state of the viewer measured by the biometric signal measurement unit and information describing an amount of data of each of the plural signals.

According to the above configuration, the transmission specification or the specification-designating signal includes information specifying a specific data format. Thus, for example, even if the transmission specification of the three-dimensional eyeglasses cannot be specified by the eyeglasses ID stored in the image display apparatus or by manufacturer or time of manufacturing, the image display apparatus can acquire (i.e., recognize) specific content of the transmission specification that may be employed by the three-dimensional eyeglasses, by receiving specific information specifying the transmission specification.

Moreover, the biometric signal measurement unit may measure electrooculogram of the viewer as the physical state of the viewer.

According to the above configuration, the electrodes mounted on the three-dimensional eyeglasses can readily and safely acquire the biometric signals of the viewer, and depending on the way of analysis, acquire many indicators obtainable from electrooculogram, such as eye movement, convergence movement, viewing direction, saccade, involuntary eye movement, and blinking. Furthermore, by utilizing the electrooculogram, viewer fatigue, a level of alertness, or viewer interest, and the like measurable.

Moreover, the biometric signal measurement unit may measure galvanic skin response or skin potential of the viewer as the physical state of the viewer.

According to the above configuration, by using the electrodes mounted on the three-dimensional eyeglasses, the state of emotional sweating is readily acquired to obtain the indicator. Furthermore, utilization of galvanic skin response allows for measurement of the level of alertness and the degree of excitement of the viewer.

Moreover, the biometric signal measurement unit may image a portion of a body of the viewer as the physical state of the viewer.

According to the above configuration, the pattern recognition through an image or the image analysis allows for acquisition of the biometric information on the viewer.

Moreover, the biometric signal measurement unit may image a vein pattern of the viewer as the physical state of the viewer.

According to the above configuration, the viewer is identified. Thus, personalized processing can be performed, such as viewing content restriction based on the viewer's age or the like or image processing such as adjustment of the depth movement based on the visual characteristics of the viewer.

Moreover, the biometric signal measurement unit may acquire a time series signal indicative of the physical state of the viewer as the biometric signal.

According to the above configuration, the temporary variations in the biometric signal can be analyzed, thereby determining the temporary variations in the physical state.

Moreover, the three-dimensional eyeglasses may further include a biometric signal processing unit configured to perform signal processing for generating the time series signal acquired by the biometric signal measurement unit as a numerical sequence, the transmitting and receiving unit included in the three-dimensional eyeglasses may transmit the numerical sequence acquired by the biometric signal processing unit to the image display apparatus, and the image display apparatus may further include a viewer state determination unit configured to determine the physical state of the viewer, based on the numerical sequence transmitted from the three-dimensional eyeglasses.

According to the above configuration, the transmission of raw data from the three-dimensional eyeglasses to the image display apparatus requires no heavy-load processing in the three-dimensional eyeglasses and can reduce power consumption. Moreover, in the image display apparatus, different processing on the biometric signal can extract different many types of information items. Using electrooculogram different biological conditions, such as convergence movement, saccade, and blinking, can be extracted by different ways of processing.

Moreover, the three-dimensional eyeglasses may further include a biometric signal processing unit configured to perform signal processing on the time series signal acquired by the biometric signal measurement unit to generate a numerical value or a numerical sequence related to a body movement of the viewer, the transmitting and receiving unit included in the three-dimensional eyeglasses may transmit the numerical value or the numerical sequence acquired by the biometric signal processing unit to the image display apparatus, and the image display apparatus may further include a viewer state determination unit configured to determine the physical state of the viewer, based on the numerical value or the numerical sequence transmitted from the three-dimensional eyeglasses.

According to the above configuration, the transmission of a result of intermediate processing from the three-dimensional eyeglasses to the image display apparatus allows dividing processing between the three-dimensional eyeglasses and the image display apparatus, thereby reducing communication load between them. Moreover, data processing load in the image display apparatus can be reduced, allowing the image processing and the like to be performed in a short time.

Moreover, the three-dimensional eyeglasses may further include a biometric signal processing unit configured to perform signal processing on the time series signal acquired by the biometric signal measurement unit to generate a numerical value or a numerical sequence related to a body movement of the viewer, and determine the physical state of the viewer using the generated numerical value or the generated numerical sequence, and the transmitting and receiving unit included in the three-dimensional eyeglasses may transmit a result of determining the physical state of the viewer by the biometric signal processing unit to the image display apparatus.

According to the above configuration, the transmission of the information indicative of the physical state of the viewer from the three-dimensional eyeglasses to the image display apparatus reduces the amount of transmission data from the three-dimensional eyeglasses to the image display apparatus, and reduces the communication load between the three-dimensional eyeglasses and the image display apparatus, and the processing load in the image display apparatus. Reduction in computational load of the image display apparatus allows the image processing and the like to be performed by the image display apparatus in a short time.

Moreover, the specification-designating signal may include information specifying a data level indicative of a degree at which data included in the communication signal is to be processed, and the biometric signal processing unit may perform the signal processing, according to the data level specified by information included in the specification-designating signal transmitted from the image display apparatus.

According to the above configuration, the biometric information is processed by the three-dimensional eyeglasses at the data level determined between the image display apparatus and the three-dimensional eyeglasses, and the processed data is transmitted to the image display apparatus, thereby balancing the processing load in the image display apparatus and the three-dimensional eyeglasses, and adjusting the communication traffic between them.

Moreover, the physical state of the viewer may represent a fatigue state of the viewer.

According to the above configuration, the viewer fatigue caused by viewing the three-dimensional image can be analyzed over time, preventing eye fatigue or cognitive fatigue of the viewer, or video-induced motion sickness associated with the fatigue, unnatural stereoscopic view, and the like. Moreover, adaptive determination can be made on states having individual differences in easy fatigability, ease of getting video-induced motion sickness, or habituation to the three-dimensional image.

Moreover, the physical state of the viewer may represent individual identification of the viewer.

According to the above configuration, the individual of the viewer can be identified. Thus, personalized processing can be performed, such as viewing content restriction based on the viewer's age or the like or image processing such as adjustment of the depth movement based on the visual characteristics of the viewer.

Moreover, three-dimensional eyeglasses for being worn by a viewer over face or head and operating in cooperation with an image display apparatus, the three-dimensional eyeglasses may include: a right-eye shutter and a left-eye shutter, states of which are switchable between an open state and a closed state; a biometric signal measurement unit configured to measure a physical state of the viewer to acquire a biometric signal; and a transmitting and receiving unit configured to convert the biometric signal acquired by the biometric signal measurement unit into a communication signal and transmit the communication signal to the image display apparatus, wherein the transmitting and receiving unit may receive a specification-designating signal designating a specification, which includes at least a data format for the communication signal, transmitted from the image display apparatus, convert the biometric signal of the viewer into the communication signal, according to the specification designated by the received specification-designating signal, and transmit the communication signal to the image display apparatus.

According to the above configuration, the three-dimensional eyeglasses convert, according to a specification designated by the specification-designating signal transmitted from the image display apparatus, the biometric signal acquired by the biometric signal measurement unit included in the three-dimensional eyeglasses into the communication signal, and transmit communication signal to the image display apparatus. In other words, communication specifications such as a data format of the biometric signal which is transmitted from the three-dimensional eyeglasses to the image display apparatus are reconciled between the image display apparatus and the three-dimensional eyeglasses. Thus, in any combination of the image display apparatus and the three-dimensional eyeglasses, the biometric information on the viewer is transmitted from the three-dimensional eyeglasses to the image display apparatus in a communication format, such as a data format, in which the image display apparatus can receive the biometric information. Thus, the image display apparatus can perform various processing (such as determining a level of fatigue) based on the biometric information on the viewer.

Moreover, the three-dimensional eyeglasses may further include a transmission specification store storing at least one transmission specification which is information indicative of a specification in which the three-dimensional eyeglasses can transmit the communication signal to the image display apparatus, wherein the transmitting and receiving unit may further transmit the at least one transmission specification stored in the transmission specification store to the image display apparatus, and the image display apparatus may receive the at least one transmission specification transmitted from the three-dimensional eyeglasses, and transmit, as the specification-designating signal, a signal indicative of at least one transmission specification selected from among the received at least one transmission specification to the three-dimensional eyeglasses.

According to the above configuration, first, the three-dimensional eyeglasses transmit, to the image display apparatus, the transmission specifications that may be employed by the three-dimensional eyeglasses, and the image display apparatus that has received the transmission specifications selects a transmission specification (a transmission specification corresponding to the measurement specification) in which the image display apparatus can receive data, from among the received transmission specifications and transmits a specification-designating signal indicative of the selection result to the three-dimensional eyeglasses. Thus, the biometric signal is more assuredly transmitted from the three-dimensional eyeglasses to the image display apparatus in a data format that can be handled by both the three-dimensional eyeglasses and the image display apparatus.

It should be noted that the at least one transmission specification may include as specific information, for example: any of: information specifying a type of the biometric signal;

information specifying a level at which the biometric signal is to be processed before the three-dimensional eyeglasses transmits information to the image display apparatus; frequency of the three-dimensional eyeglasses transmitting information to the image display apparatus; a sampling frequency and an amount of data of the sampling frequency upon acquisition of the biometric signal; data accuracy and an amount of data describing the data accuracy; a time length of the biometric signal and an amount of data of the time length; and a number of an electrode to be used for processing the biometric signal and an amount of data for describing the number of the electrode; and any of: an amount of data of the biometric signal for each electrode at which the biometric signal is measured; and a type of a result of intermediate processing and an amount of data describing the result of the intermediate processing; and a type of a result of determining the physical state of the viewer and an amount of data describing the physical state.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Embodiment

Hereinafter, certain exemplary embodiments are described in greater detail with reference to the accompanying Drawings. It should be noted that the embodiments described below are each merely a preferred illustration of the present disclosure. Values, shapes, materials, components, disposition or a form of connection between the components, steps, and the order of the steps are merely illustrative, and are not intended to limit the present disclosure. The present disclosure is indicated by the appended claims. Thus, among components of the below embodiments, components not set forth in the independent claims indicating the top level concept of the present disclosure are not necessary to achieve the present disclosure but will be described as any components for preferable embodiments.

<Image Display System>

FIG. 1 is a block diagram of an image display system 100 according to the present embodiment.

The image display system 100 is an image display system which presents a three-dimensional image to a viewer and includes a three-dimensional display TV 10 and three-dimensional eyeglasses 20.

<Overview of Three-Dimensional Display TV>

The three-dimensional display TV 10 is by way of example of an image display apparatus which alternatively outputs a left-eye image and a right-eye image to be presented to the left eye and the right eye, respectively, of a viewer, and includes a content information store 110, a screen control unit 120, a control signal transmission unit 130, a communication control unit 140, a transmitting and receiving unit 150, a viewer state determination unit 160, and an information presentation unit 170.

The content information store 110 stores video content items including three-dimensional images.

The content information store 110 not only stores media content items such as DVDs but also temporarily stores content information items acquired via broadcast waves or Internet distribution.

The screen control unit 120 displays (video display) video content items stored in the content information store 110 to an internal or external screen (not shown), and controls the video display in synchronization with the three-dimensional eyeglasses 20.

The control signal transmission unit 130 transmits to the three-dimensional eyeglasses 20 a control signal for synchronization of the video display and operation of shutters of the three-dimensional eyeglasses 20, based on a signal from the screen control unit 120.

The communication control unit 140 controls communications with the three-dimensional eyeglasses 20.

The transmitting and receiving unit 150 communicates with the three-dimensional eyeglasses 20 under the control of the communication control unit 140. Specifically, the transmitting and receiving unit 150 transmits a specification-designating signal to the three-dimensional eyeglasses 20 and receives a communication signal transmitted from the three-dimensional eyeglasses 20, for example. Herein, the communication signal is communication data transmitted from the three-dimensional eyeglasses 20 to the three-dimensional display TV 10, and includes a biometric signal acquired by the three-dimensional eyeglasses 20. The specification-designating signal is a signal designating a specification in the communication signal, specifically, a format (at least one of type, number, length, and order) of data that is at least included in the communication signal.

The viewer state determination unit 160 determines a viewer state such as fatigue, based on information such as a numerical sequence received from the three-dimensional eyeglasses 20. In the present embodiment, the viewer state determination unit 160 determines the fatigue state of the viewer. Alternatively or additionally, based on the biometric signal acquired by the three-dimensional eyeglasses 20 (specifically, a biometric signal sensor 240), the viewer state determination unit 160 may determine at least one of the following: a level of alertness; the degree of excitement; and concentration of a viewer from at least one of galvanic skin response, pulse wave, blood flow, blood-oxygen level, skin temperature, and the like. Moreover, health may be determined based on at least one of skin moisture level, blood-oxygen level, skin temperature, and the like. Moreover, a degree of video-induced motion sickness may be determined from at least one of galvanic skin response, pulse wave, skin temperature, electrooculogram, a video of the eyes, and the like. Moreover, the individual of the user may be identified based on at least one of eye image and nose vein pattern.

The information presentation unit 170 presents, on the screen, information indicative of the viewer state determined by the viewer state determination unit 160.

<Overview of Three-Dimensional Eyeglasses>

The three-dimensional eyeglasses 20 are used by a viewer to view a three-dimensional video presented on the three-dimensional display TV 10. Specifically, the three-dimensional eyeglasses 20 have a left-eye shutter and a right-eye shutter, which are worn by a viewer over the face or the head, set the left-eye shutter to an open state when the left-eye image is displayed on the three-dimensional display TV 10, and set the right-eye shutter to the open state when the right-eye image is displayed on the three-dimensional display TV 10.

The three-dimensional eyeglasses 20 include a control signal reception unit 210, a shutter control unit 220, a communication control unit 230, the biometric signal sensor 240, a state signal generation unit 250, a transmission specification store 260, and a transmitting and receiving unit 270, in addition to the eyeglasses, the left-eye shutter, and the right-eye shutter.

The control signal reception unit 210 receives the control signal, transmitted from the three-dimensional display TV 10 (to be accurate, the control signal transmission unit 130), for synchronization of the video display in the three-dimensional display TV 10 and the shutter operation of the three-dimensional eyeglasses 20.

Based on the signal from the control signal reception unit 210, the shutter control unit 220 opens and closes the right-eye shutter and the left-eye shutter (not shown) in synchronization with the right-eye image or the left-eye image displayed on the screen of the three-dimensional display TV 10.

The biometric signal sensor 240 is by way of example of a biometric signal measurement unit which measures a physical state of the viewer to acquire the biometric signal, and acquires a biometric signal of the viewer. In the present embodiment, the biometric signal sensor 240 includes electrodes for measuring electrooculograms. It should be noted that the biometric signal sensor 240 is not limited to include the electrodes for measuring electrooculograms, and may include electrodes for measuring galvanic skin response or skin moisture level, electrodes for measuring skin potential, a temperature sensor for measuring skin temperature, an infrared or near-infrared sensor for measuring pulse wave, blood flow, or blood-oxygen level, a camera or infrared camera for imaging the eyes, a near-infrared camera for imaging nose vein pattern, or the like.

The state signal generation unit 250 performs signal processing described below on data acquired by the biometric signal sensor 240 to generate a signal for use in determining the viewer state.

The transmission specification store 260 is a storage unit storing at least one transmission specification which is information indicative of a specification in which the three-dimensional eyeglasses 20 can transmit a communication signal (communication data which includes the biometric signal) to the three-dimensional display TV 10. In the present embodiment, the transmission specification store 260 stores information (i.e., the transmission specification) which designates a specification, of a signal, which is used in determining the viewer state and in which the three-dimensional eyeglasses 20 can output the signal.

The communication control unit 230 controls communications with the three-dimensional display TV 10.

The transmitting and receiving unit 270 communicates with the three-dimensional display TV 10 under the control of the communication control unit 230. Specifically, the transmitting and receiving unit 270 converts the biometric signal acquired by the biometric signal sensor 240 (to be accurate, the signal generated by the state signal generation unit 250) into the communication signal and transmits the communication signal to the three-dimensional display TV 10. Here, the transmitting and receiving unit 270 receives the above-described specification-designating signal which is transmitted from the three-dimensional display TV 10, and, according to a specification designated by the received specification-designating signal, converts the biometric signal into the communication signal and transmits the communication signal to the three-dimensional display TV 10. In other words, the transmitting and receiving unit 270 refers to the transmission specification store 260 to specify a transmission specification corresponding to the received specification-designating signal, and, according to the specified transmission specification, converts the biometric signal into the communication signal. Prior to the reception of the specification-designating signal, the transmitting and receiving unit 270 transmits to the three-dimensional display TV 10 an eyeglasses ID, which is a signal identifying the three-dimensional eyeglasses 20, and at least one transmission specification stored in the transmission specification store 260.

In the present embodiment, the transmitting and receiving unit 150 and the transmitting and receiving unit 270 wirelessly communicate with each other. A bidirectional communication is employed for the communication, which uses, for example, a radio frequency (RF) communication, a Bluetooth communication, ZigBee, a Wi-Fi communication, or an infrared communication.

Figure 2:
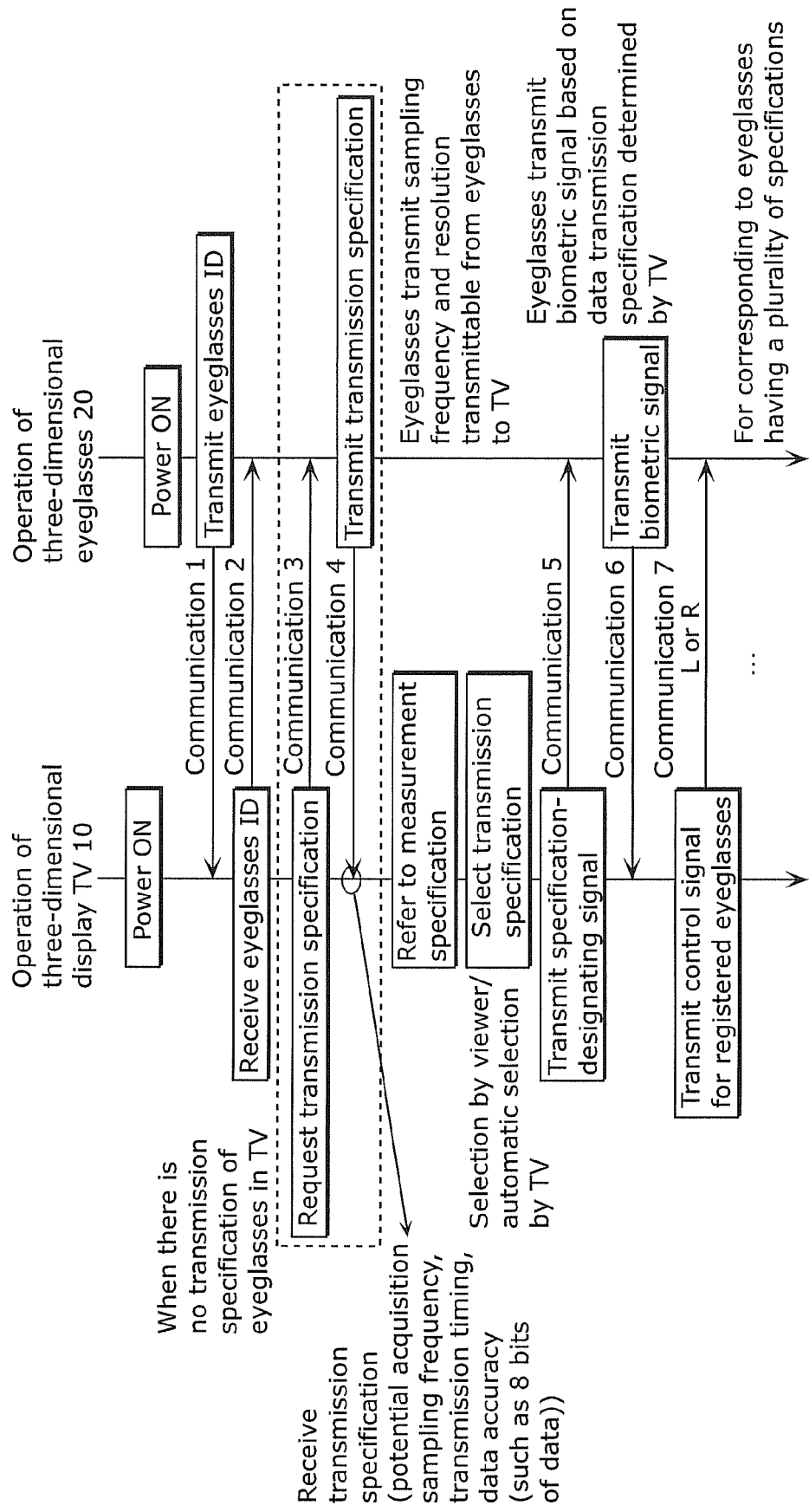
FIG. 2 is a diagram showing the methodology of communications between a three-dimensional display TV and three-dimensional eyeglasses in the image display system according to the embodiment.
Figure 3:
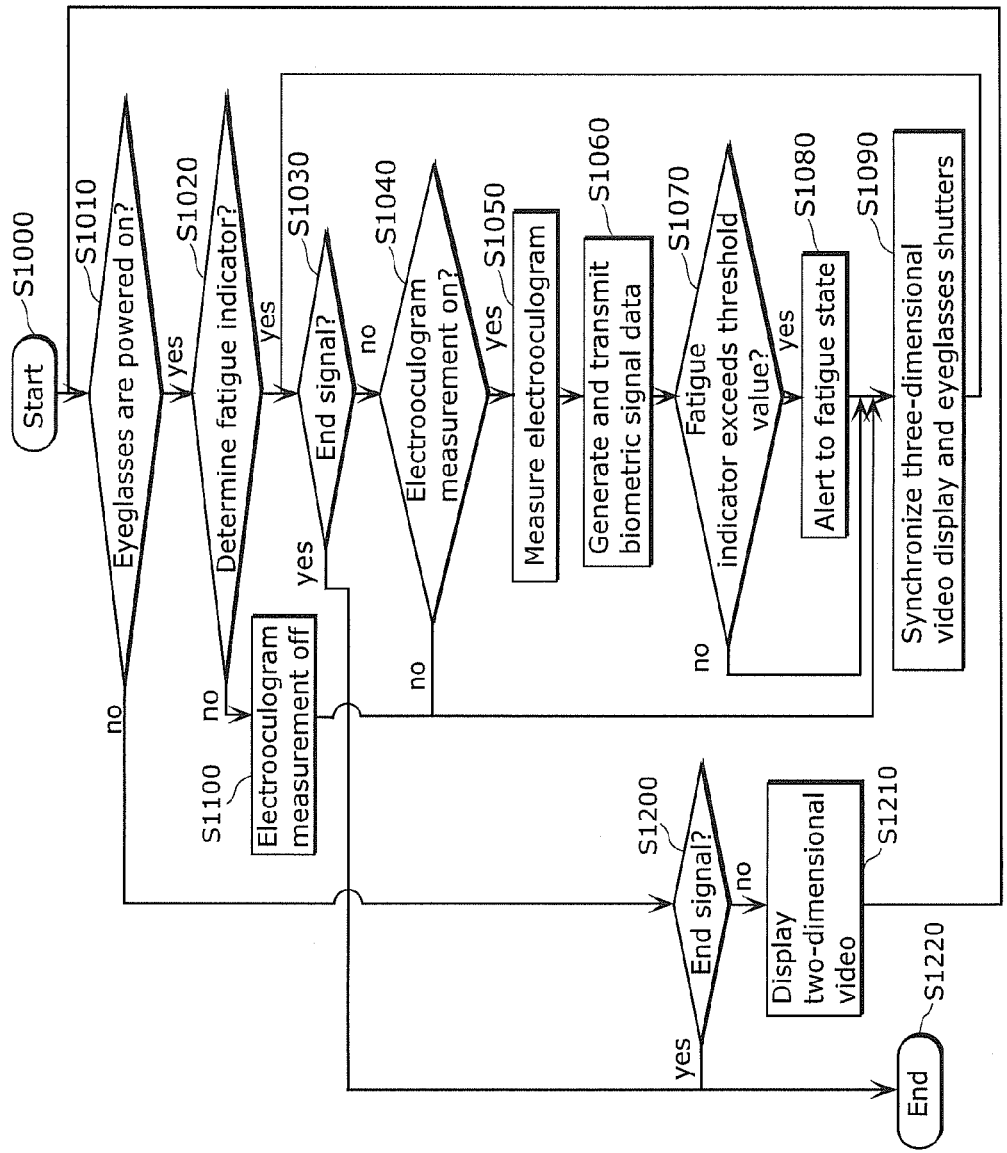
FIG. 3 is a flowchart illustrating a processing flow of the image display system according to the embodiment.

FIG. 2 is a diagram showing an example of a communication procedure between the three-dimensional display TV 10 and the three-dimensional eyeglasses 20 according to the present embodiment. FIG. 3 is a flowchart illustrating operation of the image display system 100 according to the present embodiment. Procedure of the image display system 100 according to the present embodiment will be described with reference to FIGS. 2 and 3. It should be noted that the "three-dimensional display TV 10" is simply described "TV" and the "three-dimensional eyeglasses 20" is simply described "eyeglasses" in FIGS. 2 and 3 (likewise in subsequent figures).

First, a power switch (not shown) of the three-dimensional display TV 10 is depressed by a viewer, powering on the three-dimensional display TV 10, and the image display system 100 initiates its operation (S1000).

Subsequently, the three-dimensional display TV 10 checks if the three-dimensional eyeglasses 20 are powered on (S1010). In FIG. 2, after the three-dimensional display TV 10 is powered on, a power switch (not shown) of the three-dimensional eyeglasses 20 is depressed by the viewer, powering on the three-dimensional eyeglasses 20, and the transmitting and receiving unit 270 of the three-dimensional eyeglasses 20 transmits the eyeglasses ID of the three-dimensional eyeglasses 20 to the transmitting and receiving unit 150 of the three-dimensional display. TV 10 (communication 1). Herein, the eyeglasses ID is a signal identifying the three-dimensional eyeglasses 20 and is information whereby at least one of, for example, manufacturer name, model, product number, serial number, and unique identification of the three-dimensional eyeglasses 20 is specified. The eyeglasses ID is, as described below, stored in the transmission specification store 260 of the three-dimensional eyeglasses 20.

According to this (by the three-dimensional display TV 10 receiving the eyeglasses ID), the viewer state determination unit 160 of the three-dimensional display TV 10 confirms that the three-dimensional eyeglasses 20 are in operation, and subsequently, the transmitting and receiving unit 150 transmits an eyeglasses ID reception complete signal to the three-dimensional eyeglasses 20, based on the control of the communication control unit 140 (communication 2).

While the three-dimensional display TV 10 is powered on and then the three-dimensional eyeglasses 20 are powered on in FIG. 2, the three-dimensional eyeglasses 20 may be powered on and then the three-dimensional display TV 10 may be powered on. In so doing, when the three-dimensional eyeglasses 20 are powered on, the communication control unit 230 of the three-dimensional eyeglasses 20 repeats the communication 1 at fixed time intervals until the receipt of communication 2.

When the three-dimensional eyeglasses 20 are powered on in step S1010 (yes in S1010), the processing proceeds to step S1020. On the other hand, if the three-dimensional eyeglasses 20 are not powered on in step S1010, that is, the communication 1 is not obtained (no in S1010), the processing proceeds to step S1200.

In step S1200, the three-dimensional display TV 10 determines whether input of a viewing end signal is made by the power switch (not shown) or the like of the three-dimensional display TV 10. If the input of the viewing end signal is made in step S1200 (yes in S1200), the processing proceeds to step S1220 and the operation of the image display system 100 ends (S1220). On the other hand, if the input of the viewing end signal is not made in step S1200 (no in S1200), the processing proceeds to step S1210 and the screen control unit 120 displays a two-dimensional image on the screen (not shown) of the three-dimensional display TV 10 (S1210). Herein, the two-dimensional image is achieved by displaying either one of the left and the right images on the screen. Furthermore, the screen control unit 120 outputs to the control signal transmission unit 130 a stop transmission signal, which stops the control signal transmission unit 130 from transmitting the control signal to the three-dimensional eyeglasses 20. After a predetermined time followed by the execution of step S1210, the processing returns to step S1010.

If the three-dimensional eyeglasses 20 are powered on in step S1010 (yes in S1010), the viewer state determination unit 160 attempts to select an indicator for determining viewer's biometric information corresponding to the eyeglasses ID acquired over the communication 1 in step S1010 (S1020). In the present embodiment, a fatigue indicator for determining the fatigue state of the viewer's eye is selected as the biometric information. The selection method will be described below in detail.

If the indicator (the fatigue indicator) corresponding to the eyeglasses ID cannot be specified (i.e., selected) (no in S1020), the communication control unit 140 outputs the control signal to the transmitting and receiving unit 150, and, subsequently, according to the control signal, the transmitting and receiving unit 150 transmits to the three-dimensional eyeglasses 20 an eyeglasses specification request signal requesting a specification of the indicator (the fatigue indicator) of the three-dimensional eyeglasses 20 (i.e., a signal requesting transmission of a transmission specification that can be employed by the three-dimensional eyeglasses 20) (communication 3).

Once the transmitting and receiving unit 270 of the three-dimensional eyeglasses 20 has received the eyeglasses specification request signal from the three-dimensional display TV 10, the communication control unit 230 included in the three-dimensional eyeglasses 20 outputs the control signal to the transmitting and receiving unit 270, and, as a result, according to the control signal, the transmitting and receiving unit 270 transmits, to the three-dimensional display TV 10, the specification (i.e., the transmission specification) that is stored in the transmission specification store 260 and in which the three-dimensional eyeglasses 20 can output the indicator (the fatigue indicator) (communication 4).

FIG. 4 is a diagram showing examples of the indicator specifications (i.e., the transmission specifications) stored in the transmission specification store 260. As shown in the figure, the indicator specification includes a biometric signal type utilized ("Utilized biometric information ID"), a processing level of data ("Data level ID") to transmit, transmission frequency ("Transmission frequency"), a transmission data structure ("Data structure"), and so on. Data allocation is described in the structure of the transmission data ("Data structure"), in accordance with the content of the transmission data. For transmission of raw sensor output (i.e., raw data), for example, the transmission data structure is described which includes information allocation for transmitting the attributes of the biometric signal to transmit, such as sampling frequency, data accuracy of the biometric signal, time length of the biometric signal, number of an electrode to be utilized in processing, and information allocation of the biometric signal itself, as illustrated in "Data structure" where "Utilized biometric information ID" is "001" in FIG. 4.

In other words, each of at least one transmission specification stored in the transmission specification store 260 includes (1) any of the following: information specifying the biometric signal type; information specifying a level of processing that is performed on the biometric signal until the three-dimensional eyeglasses 20 transmit information to the three-dimensional display TV 10; the frequency of the three-dimensional eyeglasses 20 transmitting information to the three-dimensional display TV 10; a sampling frequency and an amount of data of the sampling frequency upon acquisition of the biometric signal; the data accuracy and an amount of data describing the accuracy; the time length and an amount of data of the biometric signal; and the number of an electrode for use in processing the biometric signal and an amount of data describing the number, and (2) any of the following: an amount of data of a biometric signal for each electrode measuring a biometric signal; a type of a result of intermediate processing and an amount of data describing the result of intermediate processing; and a type of a result of determining the physical state of the viewer and an amount of data describing the physical state.

As described below, the transmission specification store 260 additionally stores the eyeglasses ID of the three-dimensional eyeglasses 20.

The specification (i.e., the transmission specification), in which the three-dimensional eyeglasses 20 can output the indicator, varies for different types of three-dimensional eyeglasses, and depending on the type of three-dimensional eyeglasses, some three-dimensional eyeglasses can output a single type of the indicator, some three-dimensional eyeglasses can output multiple types of indicators, and some three-dimensional eyeglasses can output the indicators in multiple data processing levels. Examples given in FIG. 4 illustrate multiple transmission specifications that can be employed by the three-dimensional eyeglasses, that is, transmission specifications in which the three-dimensional eyeglasses can output multiple types of indicators in multiple data processing levels. In FIG. 4, "Speed of convergence and divergence movements," "Amounts of convergence and divergence movements," and "Blink rate per fixed time period" indicated by 001, 002, and 007, respectively, are biometric information ("Utilized biometric information ID") available as indicators. "Blink rate per fixed time period" indicated by "Utilized biometric information ID" being 007 has two levels indicated by 001 and 003 as "Data level ID," that is, "Raw sensor output level" and a level of fatigue which is "Determination result of viewer state," respectively. Illustrated in FIG. 4 are examples of the specifications of indicators which are obtainable from electrooculograms and measured by electrodes mounted on the three-dimensional eyeglasses 20 around the eyes. As described above, "Data level ID" is information specifying the degree of processing data that is included in the communication signal (data which includes the biometric signal) transmitted from the three-dimensional eyeglasses 20 to the three-dimensional display TV 10, that is, information specifying the degree (data level) of processing performed by the three-dimensional eyeglasses 20 on the biometric signal. In the present embodiment, "Data level ID" is set to, in order of the least degree of processing, 001 (where the data included in the communication signal is "Raw sensor output level (raw data)"), 002 (where the data included in the communication signal is "Data processed by filtering signal processing"), and 003 (where the data included in the communication signal is "Determination result of viewer state").

Figure 6:
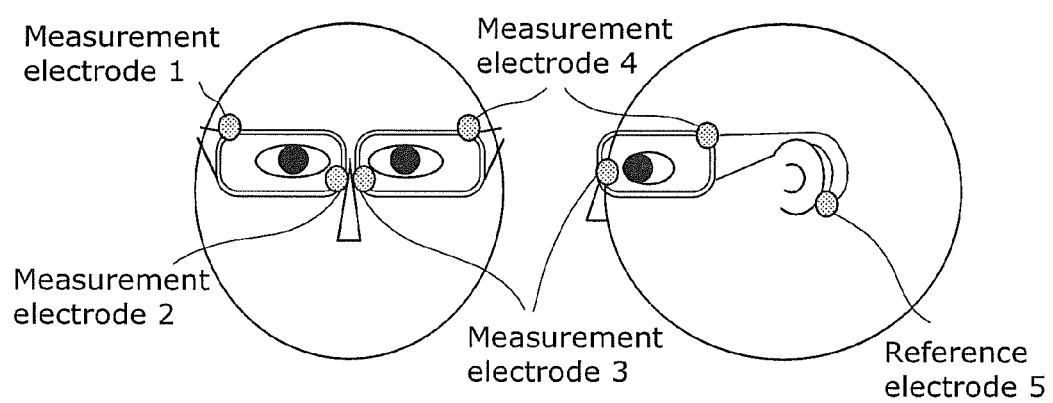
FIG. 6 is a schematic view showing an exemplary arrangement of electrodes for measuring the electrooculogram, according to the embodiment.

In FIG. 4, where "Data transmission specification ID" indicated as 001 is an example of the transmission specification where the indicator is "Change in speed of convergence and divergence movements" shown on the second row at the top of FIG. 5. Shown at the top of FIG. 5 is the fatigue indicator ("Indicator for use in fatigue detection, extractable from electrooculogram") obtainable from electrooculogram, acquisition conditions (both eyes or one eye (the number of electrodes), sampling frequency, the number of bits, and unit time (transmission time intervals)) of the biometric signal required for determination of fatigue. As indicated in "Both eyes/one eye (number of electrodes)" in FIG. 5, information on the eye movement of each eye (i.e., information on both eyes) is required to utilize "Change in speed of convergence and divergence movements" for the determination of fatigue, and six electrodes are required at a minimum to acquire the information on both eyes. The electrodes are disposed such that one eye is sandwiched by two electrodes as shown in FIG. 6, for example. Thus, six electrodes are required: four measurement electrodes 1 to 4, one reference electrode 5 and one ground electrode (not shown) for handling the potential across the viewer's body as an earth electrode. Then, as indicated in "Sampling frequency" and "The number of bits (amplitude resolution)" in FIG. 5, to capture changes in electrooculogram, in general, conditions are employed in which electrooculogram are sampled at 200 Hz or higher and digitized, and about 16 bits or greater are required as the amplitude resolution of electrooculogram. As indicated in "Unit time (communication time)" in FIG. 5, the duration of electrooculogram signals for obtaining the indicator may be up to about 5 minutes. Meanwhile, when "Data transmission specification ID" is 001, it can be seen as shown in "Data structure" in FIG. 4 that the transmission occurs once in two minutes, and electrooculogram signals for two minutes are transmitted using amounts of data allocated to the electrodes 1 through 5.

In FIG. 4, where "Data transmission specification ID" is 002 is an example of the transmission specification in which "Utilized biometric information ID" is 002, that is, "Amounts of convergence and divergence movements" is used as an indicator. The measurement conditions for utilizing "Amounts of convergence and divergence movements" in determining the fatigue are shown on the third row at the top of FIG. 5. As shown on the third row at the top of FIG. 5, data of both eyes is required to be measured using six electrodes, and the digitization needs to have the sampling frequency of 100 Hz or higher and the accuracy of 16 bits or greater. The data structure used for transmission of the data as being the raw sensor output is the same as with "Data transmission specification ID" being 001 in FIG. 4. FIG. 4 also shows a specification in which "Data level ID" is 002, that is, a specification in which data undergone the intermediate processing by the signal processing is transmitted at the intermediate output level. Depending on the type of the biometric signal or its processing scheme, the raw sensor output requires a very large amount of data, and the communication load may be high. The result of intermediate processing has, in many cases, effects in compressing information, and is effective in reducing communication load between the three-dimensional eyeglasses 20 and the three-dimensional display TV 10.

Comparison between the amount of data of the raw sensor output and the amount of data undergone the intermediate processing is shown at the bottom of FIG. 5. Shown at the bottom of FIG. 5 are the following: an amount of data at a sensor output level per unit time ("Measurement data amount per unit time") required for utilizing each biometric signal as an indicator; content of the intermediate processing ("Intermediate processing content"); and an amount of data per unit time of the result of intermediate processing ("Amount of intermediate processing result data per unit time"), with respect to the biometric signal ("Indicator for use in fatigue detection, extractable from electrooculogram") the measurement conditions of which are shown at the top of FIG. 5. FIG. 5 indicates that, when bandpass filtering; extraction of an antiphase movement in which the eyes move in opposite directions; and calculation of a total sum of differences of the extracted antiphase movements at sample points are performed as the intermediate processing on the amounts of convergence and divergence movements indicated in "Data transmission specification ID" of FIG. 4, 300000 bytes required for five minutes as time data ("Measurement data amount per unit time") for each electrode in the raw sensor output are reduced to 2 bytes ("Amount of intermediate processing result data per unit time") by calculating the total sum of the differences at sample points. By performing the intermediate processing, the transmission data structure in which, as can be seen from, for example, "Data structure" where "Data transmission specification ID" is 002 in FIG. 4, the time length obtained by measuring the biometric signal and the data accuracy at the measurement are each allocated with 2 bytes, and the movement amount calculated as the biometric signal is allocated with 2 bytes.

In FIG. 4, the transmission specification that has "Data transmission specification ID" being 003 is a transmission specification in which the biometric signal for obtaining the indicator "Blink rate per fixed time period" on the last row at the top of FIG. 5 is transmitted. The transmission specification that has "Data transmission specification ID" being 003 is a specification in which the raw sensor output is transmitted ("Data level ID" is 001), and FIG. 5 shows a specification in which the biometric signals are transmitted which are obtained at two electrodes, the measurement electrode and the reference electrode, among three electrodes (a measurement electrode, a reference electrode, and a ground electrode) used for measuring one eye.

In contrast, the transmission specification that has "Data transmission specification ID" being 004 in FIG. 4 employs blink rate per fixed time period as with the transmission specification where "Data transmission specification ID" is 003, while is a transmission specification in which "Data level ID" is 003, that is, "Determination result of viewer state" (i.e., end result of processing the biometric signal) is transmitted. The transmission specification does not require the subsequent processing. Thus, there is no need to transmit the measurement conditions, and as shown in "Data structure" of FIG. 4, only data including the level of fatigue which is the result of determining the viewer state is transmitted by 2 bytes.

The raw sensor output, the result of intermediate processing, the computational load for generating data at each data level of the state determination result, and the amount of transmission data vary depending on the indicator. The type of available indicator and the data level at the time of communication are determined depending on the specifications of the CPU and the memory of the three-dimensional eyeglasses 20 and the communication speeds of the transmitting and receiving unit 270 and the transmitting and receiving unit 150. The indicator that can be outputted by the three-dimensional eyeglasses 20 and its specification are determined upon manufacturing, according to the specifications of the CPU and the memory, communication speed, additionally, the performance and the number of sensors installed and the installation locations.

If there are multiple indicators (i.e., there are multiple measurement specifications described below) that can be outputted by the three-dimensional eyeglasses 20 and received and processed by the three-dimensional display TV 10, one indicator (i.e., measurement specification) is determined by selection by the viewer or automatic selection by the three-dimensional display TV 10. As a result, based on the control of the communication control unit 140, the transmitting and receiving unit 150 included in the three-dimensional display TV 10 transmits to the three-dimensional eyeglasses a transmission specification corresponding to the determined indicator (i.e., measurement specification) or a signal (i.e., the specification-designating signal) designating the transmission specification (communication 5). The measurement specification is by way of example of information indicative of a specification (data format) of the communication signal which is stored in a measurement specification store 163 included in, as described below, the three-dimensional display TV 10 and in which the three-dimensional display TV 10 can receive the communication signal. Herein, the measurement specification is information in which necessary biometric signal (the transmission specification which includes the data format) for each of various types of measurement on the viewer in the three-dimensional display TV 10 is provided.

When the fatigue indicator (i.e., measurement specification) is not determined in step S1020 (no in S1020), the processing proceeds to step S1100. In step S1100, the transmitting and receiving unit 150 transmits the biometric signal measurement abort signal to the three-dimensional eyeglasses 20, based on the control of the communication control unit 140. The three-dimensional eyeglasses 20 use the transmitting and receiving unit 270 to receive the biometric signal measurement abort signal, stops the operation of the biometric signal sensor 240 and the state signal generation unit 250 (S1100), the processing proceeds to step S1090, and the three-dimensional eyeglasses 20 display the three-dimensional video without measuring electrooculogram and generating a viewer state signal (S1090).

On the other hand, when the fatigue indicator is determined in step S1020 (yes in S1020), the processing proceeds to step S1030. In step S1030, the three-dimensional display TV 10 determines whether the power switch (not shown) or the like has made input of the viewing end signal. If the input of the viewing end signal is made in step S1030 (yes in S1030), the processing proceeds to step S1220, and the operation of the image display system 100 ends (S1220).

On the other hand, when there is no input of the viewing end signal in step S1030 (no in S1030), the processing proceeds to step S1040, and it is checked if the biometric signal sensor 240 and the state signal generation unit 250 are in operation (S1040). If the biometric signal sensor 240 and the state signal generation unit 250 are in operation in step S1040 (yes in S1040), the processing proceeds to step S1050. On the other hand, if the biometric signal sensor 240 and the state signal generation unit 250 are not in operation in step S1040 (no in S1040), the processing proceeds to step S1090 and the three-dimensional eyeglasses 20 display the three-dimensional video without measuring electrooculogram and generating a viewer state signal (S1090).

In step S1050, the biometric signal sensor 240 that includes the electrodes in contact with skin around the eyes acquires and stores potential fluctuations associated with the eye movement (S1050). Based on the transmission specification determined in step S1020, the state signal generation unit 250 processes the data acquired in step S1050 to generate biometric signal data to transmit. The transmitting and receiving unit 270 of the three-dimensional eyeglasses 20 transmits the biometric signal data to the three-dimensional display TV 10 (communication 6), and the transmitting and receiving unit 150 of the three-dimensional display TV 10 receives the biometric signal data (S1060). The processing level in step S1060 varies depending on the fatigue indicator determined in step S1020 and the specification of the biometric signal data. The processing levels include a level at which potential fluctuations associated with the eye movement acquired in step S1050 are directly converted into the transmission data, and a level at which the fatigue indicator is calculated and only the value of the fatigue indicator is converted into the transmission data. Thus, depending on the processing level of data communicated as the biometric signal data, the signal processing and analysis of the measured electrooculogram and the calculation of the fatigue indicator may be performed as the process of step S1060 by the state signal generation unit 250 of the three-dimensional eyeglasses 20 or may be performed as the process of step S1070 by the viewer state determination unit 160 of the three-dimensional display TV 10.

The viewer state determination unit 160 obtains the fatigue indicator from the biometric signal data that is generated in step S1060 and transmitted, to determine whether the fatigue indicator exceeds a predetermined threshold value (S1070). As a result, if the fatigue indicator exceeds the threshold value in step S1070 (yes in S1070), the information presentation unit 170 presents the fatigue state alert to the viewer (S1080). On the other hand, if the fatigue indicator is below the threshold value in step S1070 (no in S1070), the processing proceeds to step S1090.

In step S1090, the screen control unit 120 controls a screen (not shown) to display the three-dimensional video, and controls the control signal transmission unit 130 to transmit to the three-dimensional eyeglasses the control signal for closing and opening the shutters of the three-dimensional eyeglasses 20 in synchronization with the right-eye image and the left-eye image displayed on the screen (communication 7). As a result, the control signal reception unit 210 of the three-dimensional eyeglasses 20 receives the control signal transmitted from the control signal transmission unit 130, and the shutter control unit 220 closes and opens the shutters (not shown) to present the right-eye image only to the viewer's right eye and the left-eye image only to the viewer's left eye (S1090).

After a predetermined time followed by the execution of step S1090, the processing returns to step S1030 and, when the three-dimensional display TV 10 can receive the fatigue indicator that can be outputted by the three-dimensional eyeglasses 20, the three-dimensional display TV 10 monitors the level of fatigue of the viewer by repeating steps S1030 through S1090, detects signs of fatigue the viewer is unaware of, and alerts the viewer to the fatigue state. Thus, the fatigue caused by viewing the three-dimensional display TV 10, video-induced motion sickness, or unnatural stereoscopic view are prevented and the viewer can comfortably enjoy the three-dimensional video.

As described above, by the three-dimensional display TV 10 and the three-dimensional eyeglasses 20 reconciling the communication specification therebetween by a bidirectional communication, full functionality of the image display system can be achieved even if the combination of the three-dimensional display TV 10 and the three-dimensional eyeglasses 20 is different from intended upon manufacturing, such as a case where the three-dimensional display TV 10 and the three-dimensional eyeglasses 20 are made by different manufacturers, made at different times of manufacturing, or have different functions. Furthermore, reconciling the usage communication specification by the bidirectional communication can adjust computational load, load on the memory, or the commutation load, reduce battery consumption of the three-dimensional eyeglasses 20, and allows for the selection according to the viewer priority such as urgent attention, quickly responding to the viewer state.

<Details of Three-Dimensional Display TV>

Figure 7:
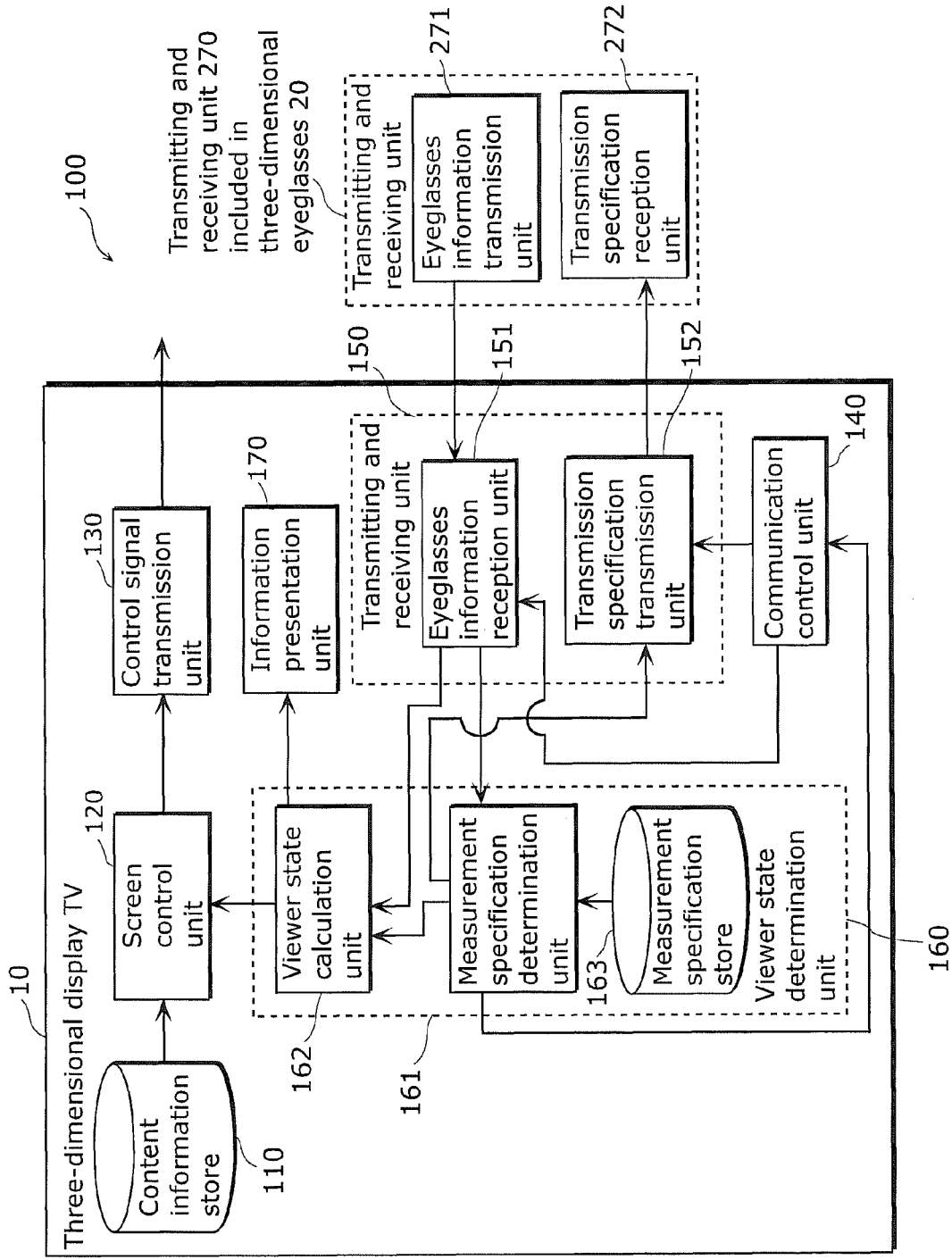
FIG. 7 is a block diagram showing an example of the detailed configuration of the three-dimensional display TV according to the embodiment.

FIG. 7 is a block diagram of the detailed three-dimensional display TV 10 according to the present embodiment. In FIG. 7, detailed configurations of the viewer state determination unit 160 and the transmitting and receiving unit 150 included in the three-dimensional display TV 10 shown in FIG. 1 and the detailed configuration of the transmitting and receiving unit 270 included in the three-dimensional eyeglasses 20 are provided, and the configurations of the other components are omitted.

The viewer state determination unit 160 includes a measurement specification determination unit 161, a viewer state calculation unit 162, and a measurement specification store 163. The measurement specification store 163 is a storage unit storing at least one measurement specification which is information indicative of a plurality of specifications in which the transmitting and receiving unit 150 can receive the communication signal (data that includes the biometric signal). Herein, the measurement specification store 163 stores a specification of the biometric signal data available for the determination of the fatigue state. The measurement specification determination unit 161 is a processing unit which determines a measurement specification used for determining the viewer state, from at least one measurement specification stored in the measurement specification store 163, determines the biometric signal based on information received from the three-dimensional eyeglasses 20 to determine the transmission specification of the biometric signal. The viewer state calculation unit 162 utilizes the biometric signal data received from the three-dimensional eyeglasses 20 to calculate or acquire the fatigue indicator of the viewer and determine the fatigue state of the viewer.

The transmitting and receiving unit 150 includes an eyeglasses information reception unit 151 and a transmission specification transmission unit 152. The eyeglasses information reception unit 151 is a reception processing unit which receives data (such as the eyeglasses ID and the communication signal) transmitted from the three-dimensional eyeglasses 20. The transmission specification transmission unit 152 is a transmission processing unit which transmits a data transmission request signal to the three-dimensional eyeglasses 20, such as a signal (the specification-designating signal) indicative of a transmission specification corresponding to the measurement specification determined by the measurement specification determination unit 161.

Figure 8:
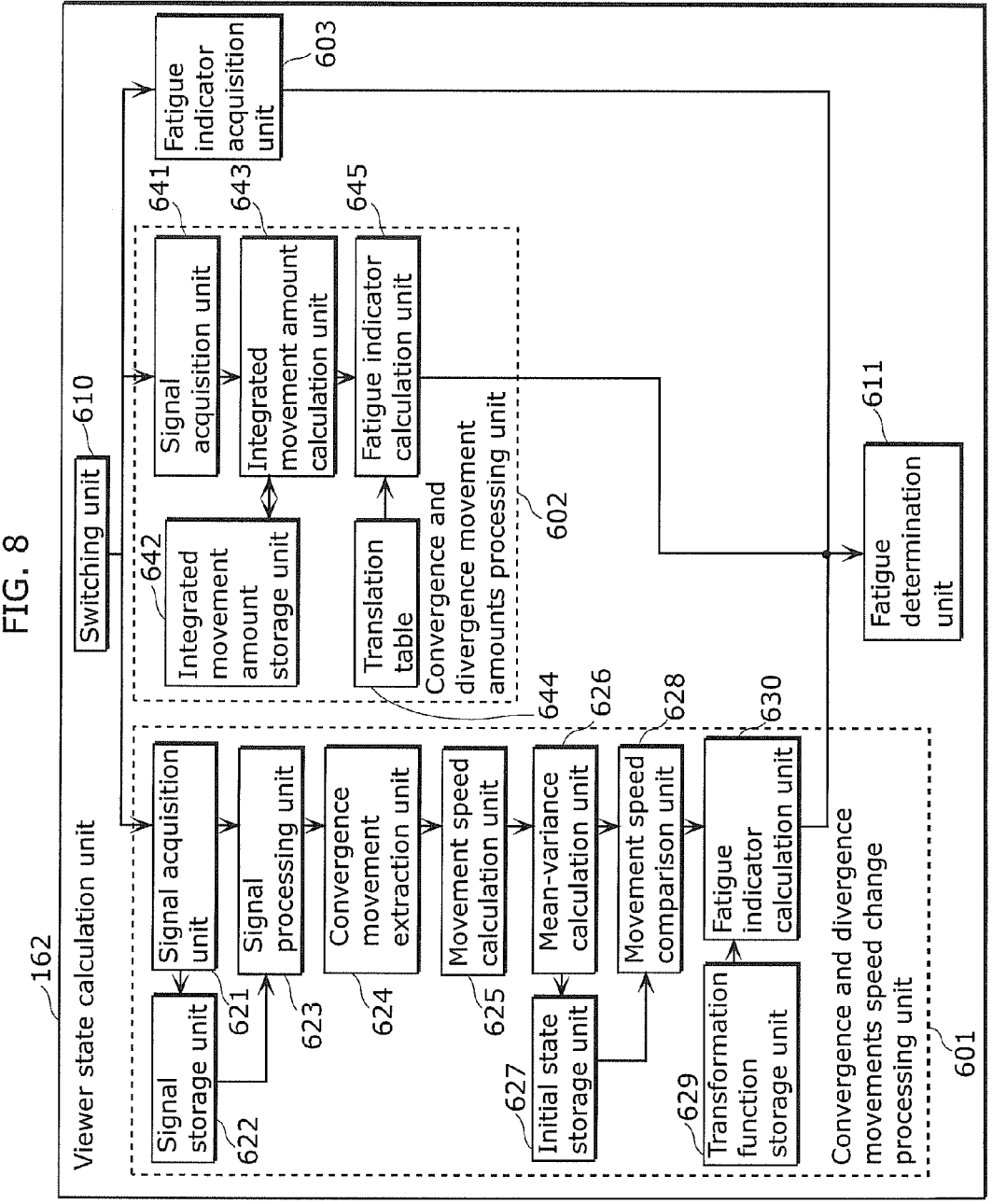
FIG. 8 is a block diagram showing an example of the detailed configuration of a viewer state calculation unit included in the three-dimensional display TV according to the embodiment.

FIG. 8 is a block diagram of the detailed viewer state calculation unit 162 depicted in FIG. 7. The viewer state calculation unit 162 includes a switching unit 610, three processing units (a convergence and divergence movements speed change processing unit 601, a convergence and divergence movement amounts processing unit 602, and a fatigue indicator acquisition unit 603) selectively executed by switching by the switching unit 610, and a fatigue determination unit 611 which determines viewer fatigue, based on the results of processing by the three processing units.

The switching unit 610 switches three processes by selecting and executing any of the three processing units (the convergence and divergence movements speed change processing unit 601, the convergence and divergence movement amounts processing unit 602, and the fatigue indicator acquisition unit 603), according to the specification of the biometric signal data utilized.

If the biometric signal data acquired by the biometric signal sensor 240 is transmitted from the three-dimensional eyeglasses 20 without being processed, the convergence and divergence movements speed change processing unit 601 utilizes the received biometric signal data to obtain the change in speed of the convergence and divergence movements of the viewer's eyes to calculate the fatigue indicator. If a total sum of the amounts of convergence and divergence movements per unit time is transmitted from the three-dimensional eyeglasses 20, the convergence and divergence movement amounts processing unit 602 integrates the received total sum of amounts of convergence and divergence movements per unit time, and converts the integrated total sum of amounts of convergence and divergence movements into the fatigue indicator. The fatigue indicator acquisition unit 603 acquires the fatigue indicator if transmitted from the three-dimensional eyeglasses 20. The fatigue determination unit 611 determines the viewer fatigue from the fatigue indicator outputted from any of the three processing units (the convergence and divergence movements speed change processing unit 601, the convergence and divergence movement amounts processing unit 602, and the fatigue indicator acquisition unit 603).

The convergence and divergence movements speed change processing unit 601 includes a signal acquisition unit 621 which acquires the received signal, a signal storage unit 622 storing the acquired signal, a signal processing unit 623, a convergence movement extraction unit 624, a movement speed calculation unit 625, a mean-variance calculation unit 626, an initial state storage unit 627 storing the viewer state at the start of viewing, a movement speed comparison unit 628 which compares the viewer state at the start of viewing and a current viewer state, a transformation function storage unit 629 storing a transformation function from the change in speed of the convergence and divergence movements to the fatigue indicator, and a fatigue indicator calculation unit 630. The convergence and divergence movement amounts processing unit 602 includes a signal acquisition unit 641, an integrated movement amount storage unit 642, an integrated movement amount calculation unit 643, a translation table 644, and a fatigue indicator calculation unit 645.

Figure 9:
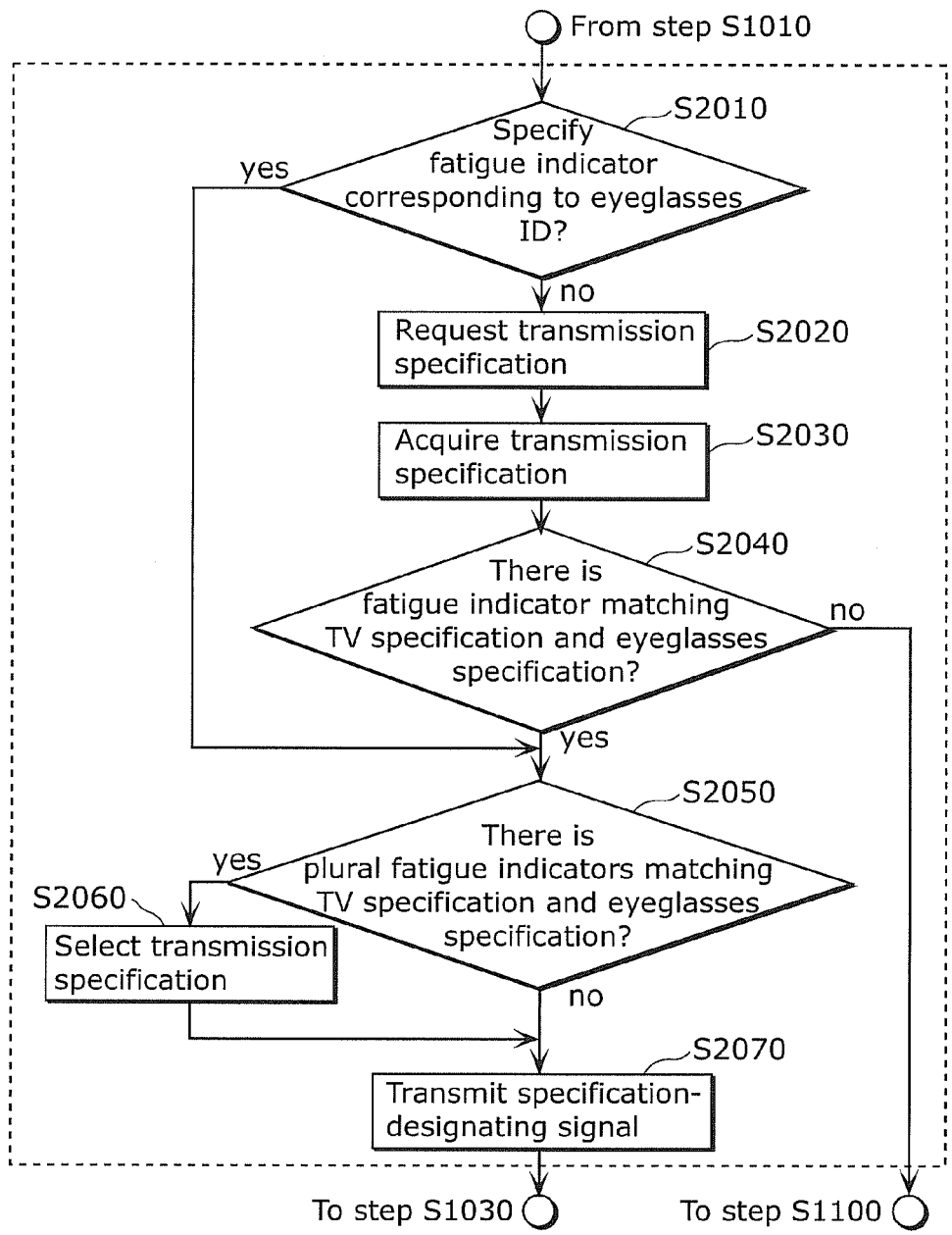
FIG. 9 is a flowchart illustrating an example of the detailed process of a fatigue indicator determination step of the processing performed by the three-dimensional display TV according to the embodiment.
Figure 10A:
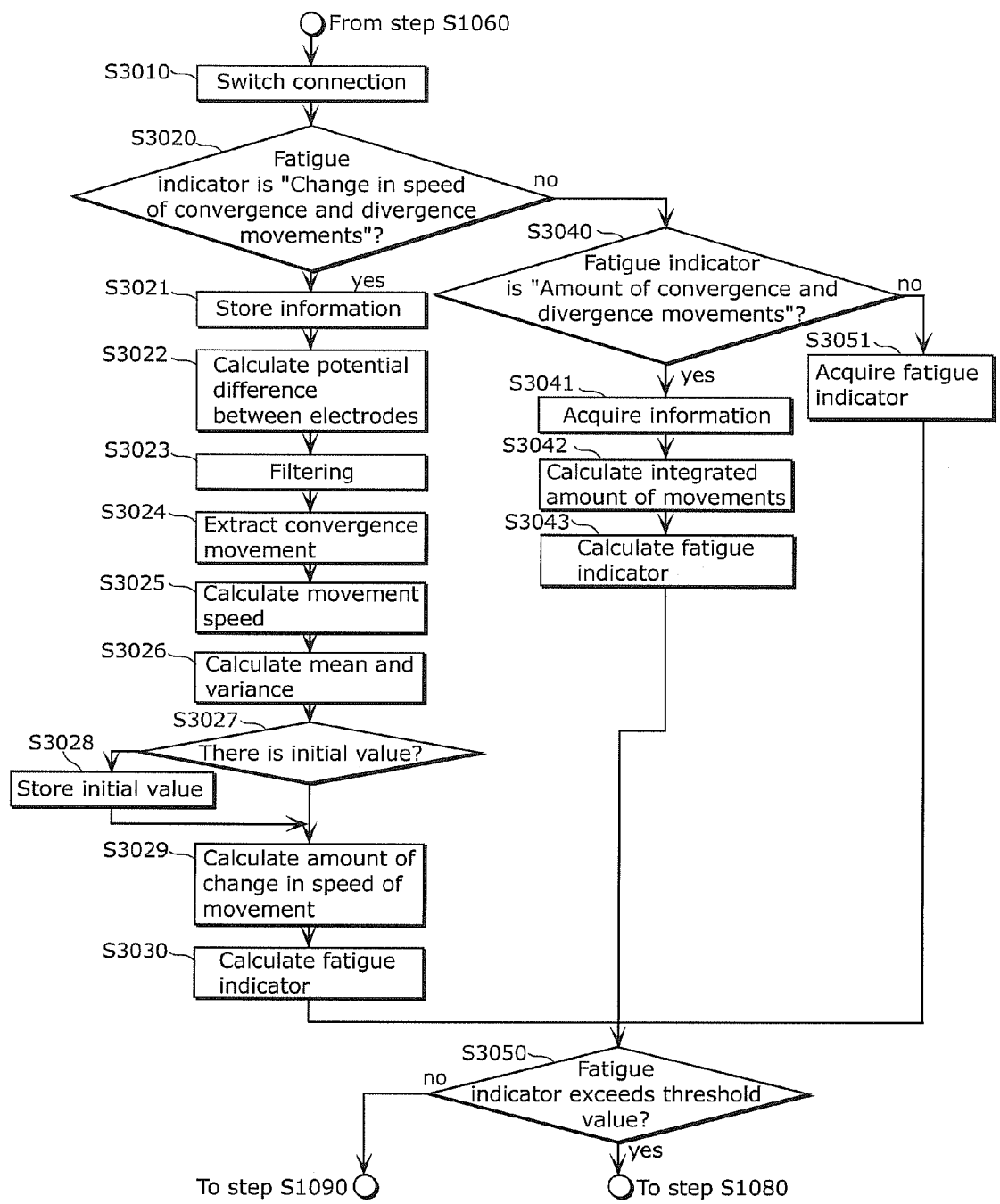
FIG. 10A is a flowchart illustrating an example of the detailed process of the fatigue indicator determination step of the processing performed by the three-dimensional display TV according to the embodiment.
Figure 10B:
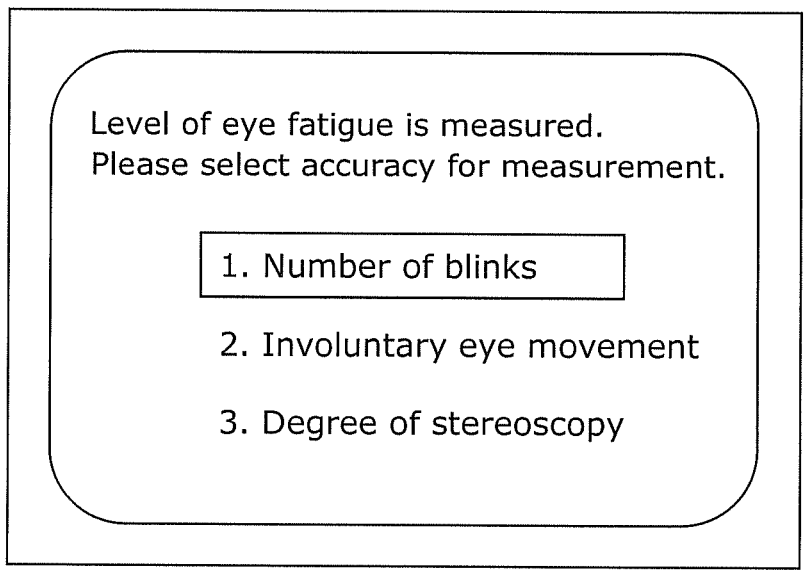
FIG. 10B is a diagram showing selection input (selection input of measurement accuracy) by a viewer in the present embodiment.

FIG. 9 is a flowchart illustrating the detailed process (the fatigue indicator determination) of step S1020 in the flowchart illustrated in FIG. 3. FIG. 10A is a flowchart illustrating the detailed process (the fatigue indicator determination) of step S1070 in the flowchart illustrated in FIG. 3. Referring to FIGS. 7 through 10A, the detailed processes of steps S1020 and S1070 of the operation of the three-dimensional display TV 10 will be described.

When it is confirmed that the three-dimensional eyeglasses 20 are powered on in step S1010, that is, the three-dimensional eyeglasses 20 transmit the eyeglasses ID and the three-dimensional display TV 10 transmits the eyeglasses ID reception complete signal to the three-dimensional eyeglasses 20, the measurement specification determination unit 161 then refers to the measurement specification store 163 to search for the biometric information utilized for the calculation of the fatigue indicator, and a transmission specification corresponding to the received eyeglasses ID (S2010). The measurement specification store 163 stores the transmission specifications ("Data transmission specification") available to the three-dimensional display TV 10 and eyeglasses IDs corresponding to the transmission specifications in, for example, a format as shown in FIG. 11A. Herein, "Eyeglasses ID" is information identifying the eyeglasses and is provided for each company and each product, for example. "Data transmission specification" is data including the transmission specification and is, herein, information including "Utilized biometric information," "Data level," and "Data structure." "Utilized biometric information" indicates the type of the biometric information utilized (for example, "Change in speed of convergence and divergence movements," "Amounts of convergence and divergence movements," or the like. "Data level" indicates the converted state (the degree of processing) of the used data, and is, for example, information specifying whether information on the sensor output is directly used or converted (processed) and used. "Data structure" indicates the actual content of the data (such as sampling frequency, data accuracy, time length, electrodes).

If there is the appropriate eyeglasses ID in the measurement specification store 163 and the biometric information utilized for the calculation of fatigue indicator and the data transmission specification are specified in step S2010 (yes in S2010), the processing proceeds to step S2050. On the other hand, if no appropriate eyeglasses ID is in the measurement specification store 163 and the biometric information utilized for the calculation of fatigue indicator and the data transmission specification are not specified in step S2010 (no in S2010), the processing proceeds to step S2020.

In step S2020, the measurement specification determination unit 161 requests the communication control unit 140 to transmit the eyeglasses specification request signal to the three-dimensional eyeglasses 20. According to the request, the communication control unit 140 outputs the control signal to the transmission specification transmission unit 152 of the transmitting and receiving unit 150. As a result, the transmission specification transmission unit 152 transmits to the three-dimensional eyeglasses 20 the eyeglasses specification request signal requesting the specification of the fatigue indicator owned by the three-dimensional eyeglasses 20 (communication 3, S2020).

In the three-dimensional eyeglasses 20, once a transmission specification reception unit 272 included in the transmitting and receiving unit 270 has received the eyeglasses specification request signal from the three-dimensional display TV 10, the communication control unit 230 of the three-dimensional eyeglasses 20 outputs the control signal to an eyeglasses information transmission unit 271 included in the transmitting and receiving unit 270. As a result, the eyeglasses information transmission unit 271 transmits to the three-dimensional display TV 10 a specification (i.e., at least one transmission specification) that is stored in the transmission specification store 260 and in which the three-dimensional eyeglasses 20 can output the fatigue indicator (the communication 4). It should be noted that the number of specifications in which the three-dimensional eyeglasses 20 can output the fatigue indicator may be one or plurality.

The eyeglasses information reception unit 151 of the three-dimensional display TV 10 receives specifications (i.e., at least one transmission specification) of the fatigue indicator transmitted from the three-dimensional eyeglasses 20 (S2030). The measurement specification determination unit 161 refers to the measurement specification store 163 to search for, among the specifications of the fatigue indicator (i.e., at least one transmission specification) acquired in step S2030, a specification that matches any of data transmission specifications (i.e., the measurement specifications) available to the three-dimensional display TV 10 (S2040).

As a result, when none of the specifications of the fatigue indicator (i.e., at least one transmission specification) acquired in step S2030 matches any data transmission specification (i.e., any measurement specification) available to the three-dimensional display TV 10 in step S2040 (no in S2040), the processing proceeds to step S1100, and the three-dimensional display TV 10 transmits the biometric signal measurement abort signal to the three-dimensional eyeglasses 20 to stop the biometric by the three-dimensional eyeglasses 20 (S1100). On the other hand, if one or more specifications of the fatigue indicator (i.e., at least one transmission specification) acquired in step S2030 match the data transmission specification (i.e., any measurement specification) available to the three-dimensional display TV 10 in step S2040 (yes in S2040), the processing proceeds to step S2050.

In step S2050, the number of data transmission specifications available to the three-dimensional display TV that match the specification in which the three-dimensional eyeglasses 20 can output the fatigue indicator is checked (S2050). As a result, when there is one data transmission specification that is available to the three-dimensional display TV 10 and matches the specification in which the three-dimensional eyeglasses 20 can output the fatigue indicator in step S2050 (no in S2050), the processing proceeds to step S2070. On the other hand, when there are two or more data transmission specifications that are available to the three-dimensional display TV 10 and match the specification in which the three-dimensional eyeglasses 20 can output the fatigue indicator in step S2050 (yes in S2050), the measurement specification determination unit 161 selects one specification from among the data transmission specifications (S2060). Among the data transmission specifications that are available to the three-dimensional display TV 10 and match the specification in which the three-dimensional eyeglasses 20 can output the fatigue indicator, the measurement specification determination unit 161 selects a specification, for example, that requires the least processing from the three-dimensional eyeglasses 20, that is, a specification in which the data level of the transmission data is the sensor output or intermediate output close to the sensor output. Alternatively, for example, the measurement specification determination unit 161 selects a data transmission specification that requires the least communication load. In this case, the measurement specification determination unit 161 selects a specification in which the fatigue indicator or a specification in which intermediate output that is close to the fatigue indicator is transmitted. For example, a screen display shown in FIG. 10B may be presented to the viewer and the selection may follow the selection input of the viewer.

After one data transmission specification is selected in step S2060, the transmission specification transmission unit 152 transmits the determined data transmission specification (i.e., the specification-designating signal) for the fatigue indicator to the three-dimensional eyeglasses, based on the control of the communication control unit 140 (communication 5). For example, assuming that the eyeglasses ID P12-34 is transmitted and the data transmission specification of FIG. 11A supports only the data transmission specification ID 001, the three-dimensional display TV 10 transmits data (i.e., the specification-designating signal; content of communication 5) shown in FIG. 11B in advance so as to receive the biometric signal data from the three-dimensional eyeglasses 20 in the specification where the data transmission specification ID is 001. In such a manner, by the three-dimensional display TV 10 transmitting, in advance, a transmission format of the biometric data or information designating the transmission, data measured by the three-dimensional eyeglasses 20 can be utilized even if the three-dimensional eyeglasses 20 are not the three-dimensional eyeglasses attached to the three-dimensional display device.

In step S1070, first, the switching unit 610 of the viewer state calculation unit 162 connects the eyeglasses information reception unit 151 and a processing unit directed toward the specification of the fatigue indicator determined in step S1020 (S3010). In the example of the present embodiment, the switching unit 610 switches the connections of the convergence and divergence movements speed change processing unit 601, the convergence and divergence movement amounts processing unit 602, and the fatigue indicator acquisition unit 603 with the eyeglasses information reception unit 151. While the switching by the switching unit 610 in step S3010 is performed after the three-dimensional display TV has received the biometric signal data in step S1060, in addition to this, the switching may be performed at any time after the specification of the fatigue indicator is determined in step S1020 and before the processing on the received biometric signal data is performed in step S1070.

The viewer state calculation unit 162 checks whether the fatigue indicator is "Change in speed of convergence and divergence movements" (S3020). When the fatigue indicator is "Change in speed of convergence and divergence movements" (yes in S3020), the signal acquisition unit 621 of the convergence and divergence movements speed change processing unit 601 acquires the biometric signal data from the eyeglasses information reception unit 151 and stores the biometric signal data in the signal storage unit 622 (S3021). On the other hand, when the fatigue indicator is not "Change in speed of convergence and divergence movements" in step S3020 (no in S3020), the viewer state calculation unit 162 checks if the fatigue indicator is "Amount of convergence and divergence movements" (S3040). When the fatigue indicator is "Amount of convergence and divergence movements" (yes in S3040), the signal acquisition unit 641 of the convergence and divergence movement amounts processing unit 602 acquires the biometric signal data from the eyeglasses information reception unit 151 (S3041). On the other hand, when the fatigue indicator is not "Amount of convergence and divergence movements" in step S3040 (no in S3040), the fatigue indicator acquisition unit 603 acquires the biometric signal data from the eyeglasses information reception unit 151, and the processing proceeds to step S3050.

Subsequently, the processing of steps S3022 through S3030 is performed by the convergence and divergence movements speed change processing unit 601. The convergence and divergence movements speed change processing unit 601 selects the example utilizing the change in speed of the convergence and divergence movements, among the examples of the fatigue determination using the biometric signal shown in FIG. 5, that is, the three-dimensional eyeglasses 20 select the specification in which the data is transmitted without the signal processing, thereby reducing the computational load of the three-dimensional eyeglasses 20 and the amount of memory. This reduces the cost of the three-dimensional eyeglasses 20 and power consumption, allowing for the long-term use of the three-dimensional eyeglasses 20. Moreover, reducing the battery size (battery capacity) can provide increased design flexibility and lightweight eyeglasses. Furthermore, by the three-dimensional display TV 10, free of the battery capacity problem and having extra computing power and extra memory capacity, performing detailed signal processing can determine the fatigue at high accuracy.

Figures 11B, 12:
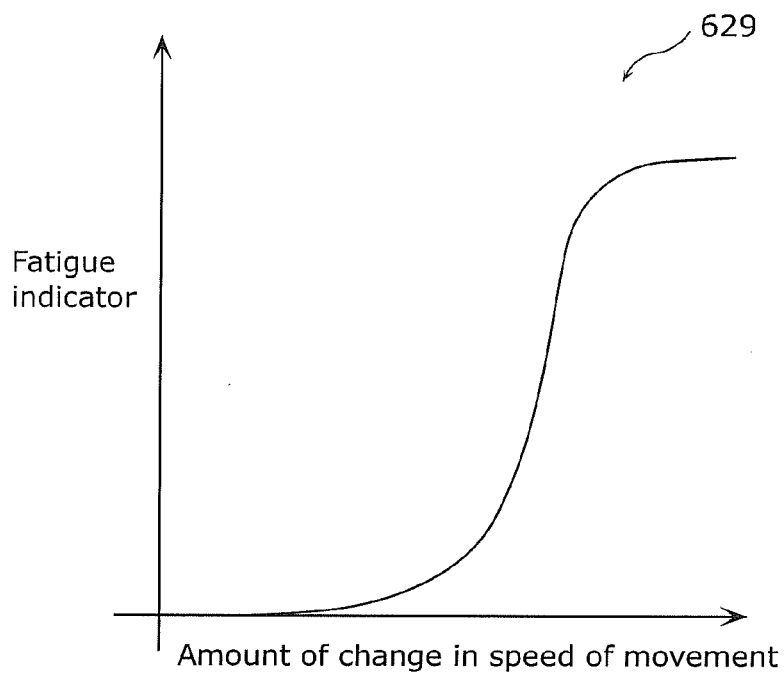
FIG. 11B is a diagram showing example data of a specification-designating signal which is transmitted by the three-dimensional display TV according to the embodiment.
FIG. 12 is a graph showing an example of a transformation function stored in a transformation function storage unit according to the embodiment.

The biometric signal data acquired in step S3021 is potential data at each of the electrodes disposed on the three-dimensional eyeglasses 20 as illustrated in FIG. 6. It should be noted that the ground electrode is provided on the right temple tip (not shown) of the three-dimensional eyeglasses 20. The signal processing unit 623 calculates a potential difference between each of the four measurement electrodes 1 to 4 provided in contact with the skin around the eyes and the reference electrode 5 provided on the temple tip (S3022). Furthermore, the signal processing unit 623 passes the potential difference data between the reference electrode 5 and each of the measurement electrodes 1 to 4 calculated in step S3022, through a band pass filter (S3023). The band pass filter is, for example, a filter having a passband of 10 Hz to 100 Hz. The convergence movement extraction unit 624 calculates a difference between a potential difference between the measurement electrode 1 and the reference electrode 5 and a potential difference between the measurement electrode 4 and the reference electrode 5, as a component of movement in the horizontal direction common to both eyes. The convergence movement extraction unit 624 also calculates a difference between the mean of the potentials at the measurement electrode 1 and the measurement electrode 4 and the mean of the potentials at the measurement electrode and the measurement electrode 3, as a component of movement in the vertical direction common to both eyes. Furthermore, the convergence movement extraction unit 624 obtains a difference between the potentials at the measurement electrode 1 and the measurement electrode 2 and a difference between the potentials at the measurement electrode 4 and the measurement electrode 3, subtracts the components of movements in the horizontal and vertical directions that are common to both eyes from each of the difference of the potentials between the measurement electrode 1 and the measurement electrode 2 and the difference of the potentials between the measurement electrode 4 and the measurement electrode 3, to extract a component of the viewer's right eye convergence movement between the measurement electrode 1 and the measurement electrode 2 and a component of the viewer's left eye convergence movement between the measurement electrode 3 and the measurement electrode 4 (S3024). The movement speed calculation unit 625 divides a potential difference between a peak and the following peak for all peaks of the potential fluctuations of the component of each of the left and right eye convergence movements extracted in step S3024 by a time between the peaks to calculate the movement speed of each of the left and the right eyes as a movement speed (S3025). The mean-variance calculation unit 626 calculates the mean and the variance, of the movement speed between the peaks which is calculated in step S3025, for a full time range of the data acquired in step S3021 (S3026). The mean-variance calculation unit 626 checks if the initial value of the movement speed at the start of viewing is stored in the initial state storage unit 627 (S3027). If the initial value is stored in the initial state storage unit 627 in step S3027 (yes in S3027), the processing proceeds to step S3029. On the other hand, if the initial value is not stored in the initial state storage unit 627 in step S3027 (no in S3027), the mean-variance calculation unit 626 outputs the values of the mean and the variance of the movement speed calculated in step S3026 to the initial state storage unit 627. Then, the initial state storage unit 627 stores therein the values of the mean and the variance of the movement speed calculated in step S3026 (S3028). The movement speed comparison unit 628 obtains a difference between the mean of the movement speed calculated in step S3026 and the mean of the movement speed stored in the initial state storage unit 627 to obtain a difference between the variance of the movement speed calculated in step S3026 and the variance of the movement speed stored in the initial state storage unit 627. Then, the mean difference and the variance difference are multiplied by constants and added together, calculating the added value as an amount of change in speed of movement (S3029). The fatigue indicator calculation unit 630 refers to the transformation function of the calculated amount of change in speed of movement which is stored in the transformation function storage unit 629, to calculate the fatigue indicator (S3030). The transformation function is a function indicating the relationship between the amount of change in speed of movement and the fatigue indicator, for example, as shown in FIG. 12.

Next, the processing of the convergence and divergence movement amounts processing unit 602 will be described. The convergence and divergence movement amounts processing unit 602 processes the example utilizing the amounts of convergence and divergence movements, among the examples of the fatigue determination using the biometric signal shown in FIG. 5. Herein, the three-dimensional eyeglasses 20 perform the signal processing and select the transmission specification in which data is transmitted to the three-dimensional display TV 10. The amounts of convergence and divergence movements utilized for the fatigue determination are the total sum of the convergence movements in a fixed time interval. In the signal processing, computational load of the signal processing is small and the total sum of the convergence movements with respect to the potential data, which is a time waveform, is one numerical value. Thus, the signal processing significantly compresses the amount of data. This can significantly reduce the communication load. The processing required in the three-dimensional display TV 10 is small and simultaneous viewing by a large number of viewers can be accommodated.

Figure 13:
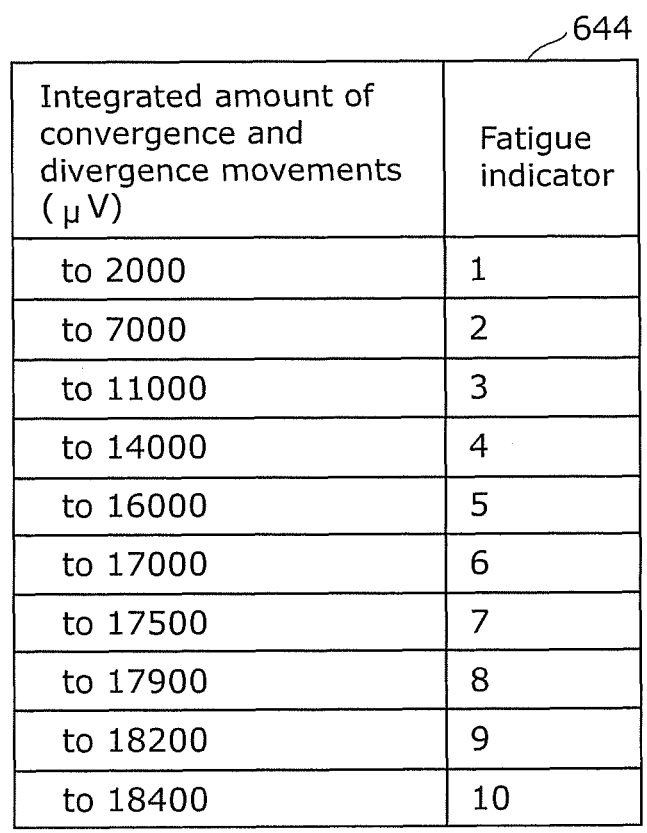
FIG. 13 is a diagram showing an example of data stored in a translation table according to the embodiment.

The biometric signal acquired in step S3041 is obtained as the operation of the three-dimensional eyeglasses 20 from the electrooculogram by a method described below. The biometric signal includes a total sum of the convergence and divergence movements in the fixed time interval obtained from electrooculogram. The integrated movement amount storage unit 642 stores an integrated value of the convergence and divergence movements from the start time of viewing the three-dimensional video. The integrated movement amount calculation unit 643 calculates a sum of the total sum, per unit time, of the convergence and divergence movements acquired in step S3041 and the integrated value, stored in the integrated movement amount storage unit 642, of the convergence and divergence movements from the start time of viewing the three-dimensional video to the signal acquisition, to calculate the up-to-date integrated value of the convergence and divergence movements including the convergence and divergence movements indicated by the newly acquired signals, and store the obtained up-to-date integrated value into the integrated movement amount storage unit 642 (S3042). The fatigue indicator calculation unit 645 refers to the translation table 644 to specify a fatigue indicator corresponding to the calculated integrated value of the convergence and divergence movements, thereby calculating the fatigue indicator (S3043). The translation table 644 is, for example, a table storing the correspondence between "Fatigue indicator" and the range of the integrated value of the convergence and divergence movements ("Integrated amount of convergence and divergence movements") as shown in FIG. 13.

Next, the processing of the fatigue indicator acquisition unit 603 will be described. The fatigue indicator acquisition unit 603 processes the example utilizing blink rate per fixed time period, among the examples of the fatigue determination using the biometric signal shown in FIG. 5. Herein, the specification is selected in which the three-dimensional eyeglasses 20 calculate up to the fatigue indicator, and data indicating the calculation result is transmitted to the three-dimensional display TV 10. The blink rate utilized for the fatigue determination is the number of blinks in the fixed time interval. The blinking is easy to detect because the potential is significantly large as compared to the electrooculogram by eye movement. Thus, the blinking is detectable even if the resolution (the accuracy) of the amplitude of the potential at the measurement is low. Thus, the amount of data required from the processing of the three-dimensional eyeglasses 20 decreases, and the computational load and also the memory may decrease. Thus, although up to the fatigue indicator is calculated by the three-dimensional eyeglasses 20, reduced computing power and a reduced memory capacity are required, thereby reducing cost. Furthermore, since simply the value of the fatigue indicator is calculated rather than time data, the communication load decreases. Moreover, there is little processing performed in the three-dimensional display TV 10, and viewing by a large number of people can be accommodated.

The fatigue indicator acquisition unit 603 acquires the biometric signal as the fatigue indicator in step S3051.

The fatigue determination unit 611 compares the fatigue indicator calculated in step S3030 or S3043 or the fatigue indicator acquired in step S3051 with a predetermined threshold value (S3050). Assuming that the threshold value is, for example, 5, when the fatigue indicator is greater than or equal to 5 (no in S3050), the processing proceeds to step S1080, while when the fatigue indicator is less than 5 (yes in S3050), the processing proceeds to step S1090.

In this way, the three-dimensional display TV 10 receives the biometric signal transmitted from the three-dimensional eyeglasses 20 in a communication specification (i.e., the transmission specification), in which the three-dimensional eyeglasses 20 can transmit the biometric signal, and determines the fatigue state of the viewer from the received biometric signal. Because of this, by supporting the plurality of communication specifications of the biometric signal, even if the three-dimensional image is viewed by a viewer using eyeglasses made by different manufacturer or made at different time of manufacturing or eyeglasses having different model from those of the three-dimensional display TV 10, the three-dimensional display TV 10 can acquire the biometric signal corresponding to the three-dimensional eyeglasses 20 in use by the viewer, and determine the fatigue state of the viewer, assuring the viewer of comfortable viewing of the three-dimensional image.

<Details of Three-Dimensional Eyeglasses>

Figure 14:
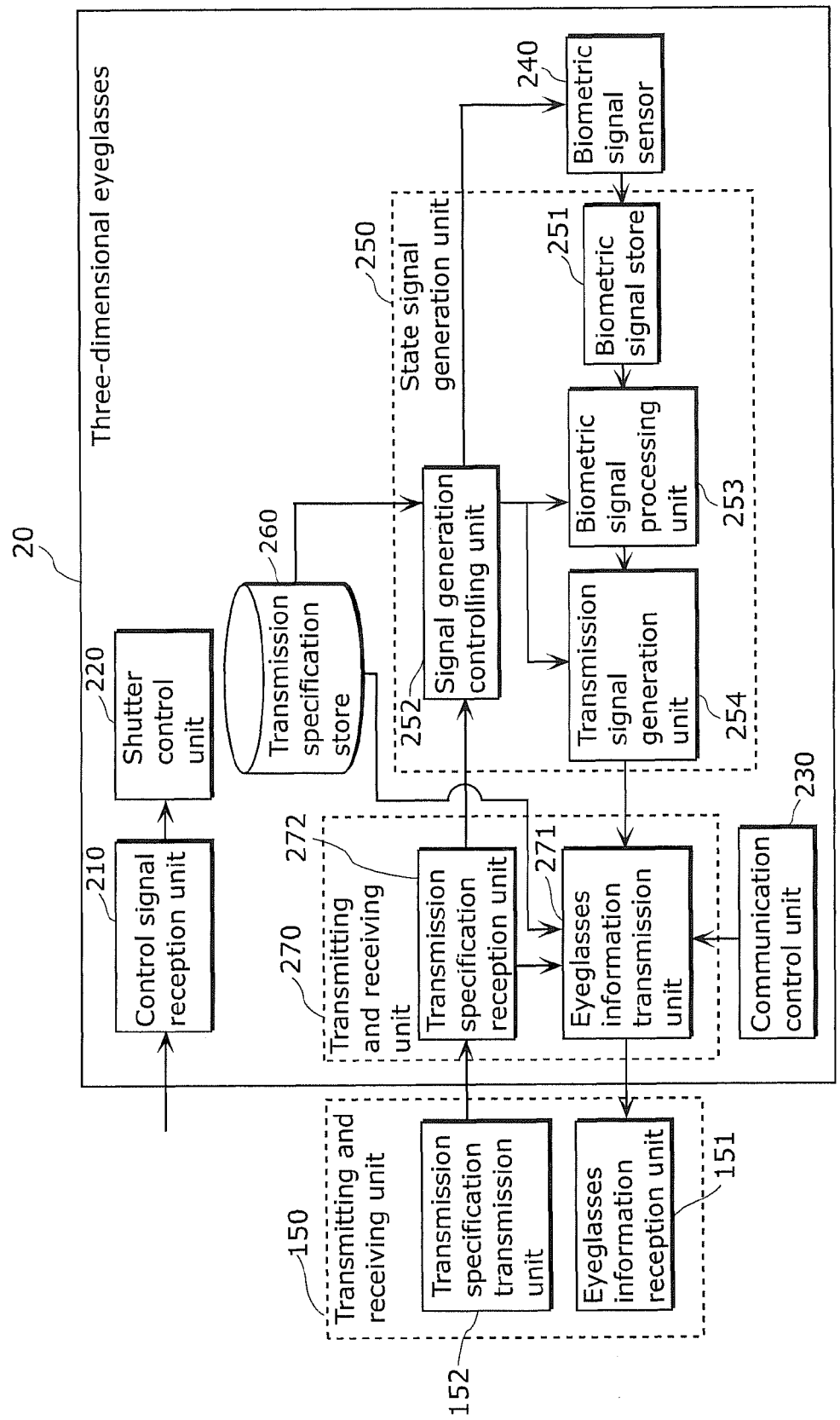
FIG. 14 is a block diagram showing an example of the detailed configuration of the three-dimensional eyeglasses according to the embodiment.

FIG. 14 is a block diagram of the three-dimensional eyeglasses 20 in detail. FIG. 14 shows detailed configurations of the state signal generation unit 250 and the transmitting and receiving unit 270 included in the three-dimensional eyeglasses 20 shown in FIG. 1. The transmitting and receiving unit 150 included in the three-dimensional display TV 10 and the detailed configuration are provided, and the configurations of the other components are omitted.

The state signal generation unit 250 includes a biometric signal store 251, a signal generation controlling unit 252, a biometric signal processing unit 253, and a transmission signal generation unit 254. The potential data for each electrode measured by the biometric signal sensor 240 is accumulated in the biometric signal store 251. The signal generation controlling unit 252 controls the specification of the transmission data, based on the specification received by the transmission specification reception unit 272 that have been requested from the three-dimensional display TV 10. The biometric signal processing unit 253 performs processing on the biometric signal accumulated in the biometric signal store 251, based on the control of the signal generation controlling unit 252. The transmission signal generation unit 254 generates the transmission data (i.e., the communication signal) which includes the biometric signal, based on the control of the signal generation controlling unit 252.

Figure 15:
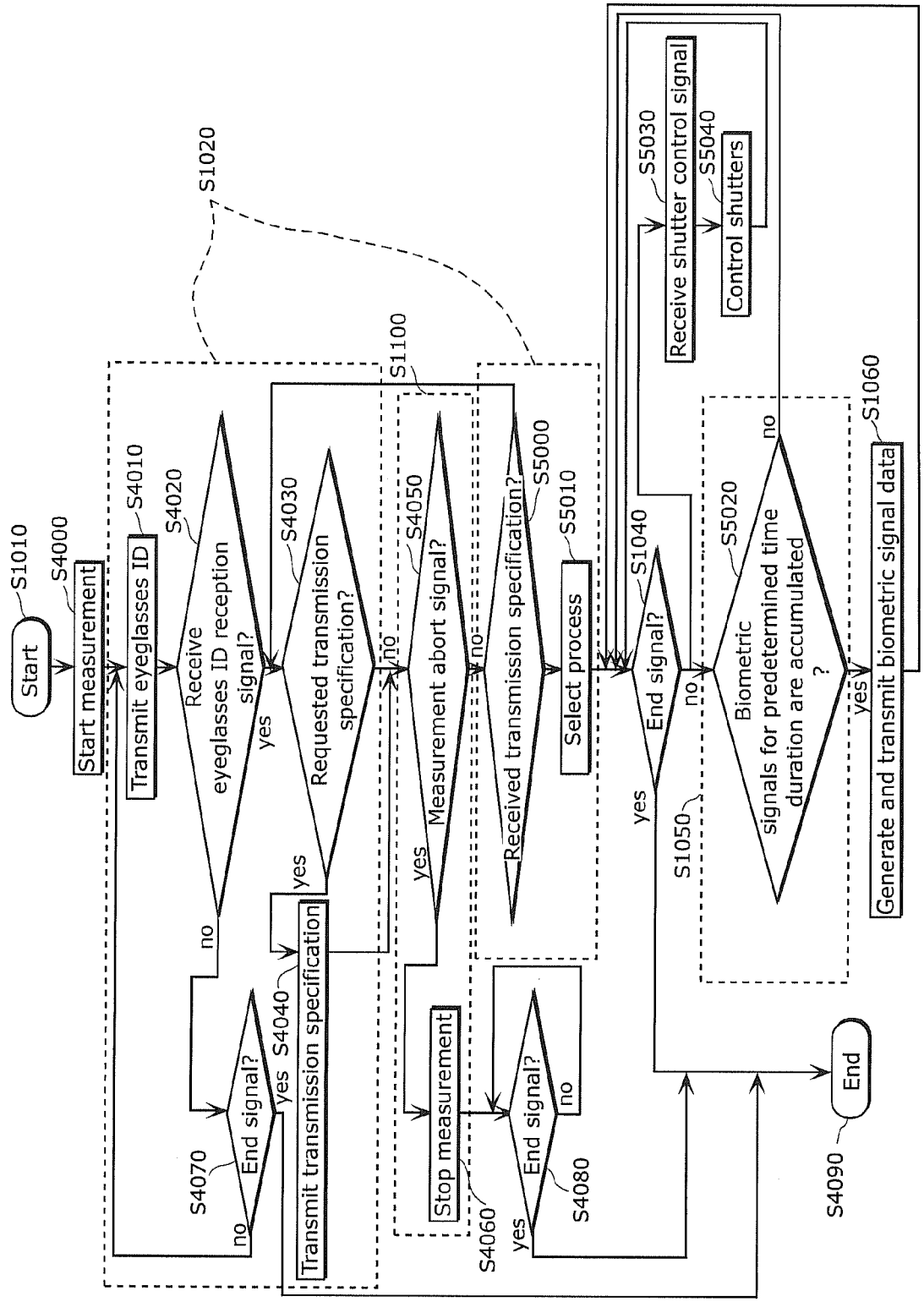
FIG. 15 is a flowchart illustrating an example of a processing flow of the three-dimensional eyeglasses according to the embodiment.

FIG. 15 is a flowchart illustrating the processing of the three-dimensional eyeglasses 20. The same processes as in FIG. 3 are referred to by the same step numbers.

The operation of the three-dimensional eyeglasses 20 will be described with reference to FIGS. 14 and 15, and FIG. 2 illustrating the communication procedure.

First, the three-dimensional eyeglasses 20 are powered on by input by the power switch (not shown) (S1010). The biometric signal sensor 240 starts measuring the biometric signal of the viewer, accumulating the measurement result in the biometric signal store 251 (S4000). The eyeglasses information transmission unit 271 transmits the eyeglasses ID of the three-dimensional eyeglasses 20 stored in the transmission specification store 260, according to the control of the communication control unit 230 (communication 1, S4010). The data (the transmission specification) stored in the transmission specification store 260 is, for example, data (Example A or Example B) as shown in FIG. 16. Herein, two sets of the eyeglasses ID of the three-dimensional eyeglasses 20 and at least one transmission specification that can be employed by the three-dimensional eyeglasses 20 (two example sets) are shown. Example A shown in FIG. 16 gives a transmission specification example where there is one specification in which the three-dimensional eyeglasses 20 can transmit the biometric signal, and Example B of FIG. 16 shows a transmission specification example where there are plural specifications in which the three-dimensional eyeglasses 20 can transmit the biometric signal. In step S4010 (communication 1), the eyeglasses information transmission unit 271 reads out the eyeglasses ID from the transmission specification store 260 and transmits the eyeglasses ID to the three-dimensional display TV 10.

Thereafter, the transmission specification reception unit 272 checks if the three-dimensional eyeglasses 20 have received the eyeglasses ID reception signal (a signal indicative of the reception of the eyeglasses ID) from the three-dimensional display TV 10 (communication 2, S4020). If the eyeglasses ID reception signal is received (yes in S4020), the processing proceeds to step S4030. On the other hand, if the eyeglasses ID reception signal is not received (no in S4020), the transmission specification reception unit 272 checks if an end signal is present (S4070). The end signal is inputted to the transmission specification reception unit 272 by input of the power switch (not shown) powering off the three-dimensional eyeglasses 20. Alternatively, the end signal is inputted to the transmission specification reception unit 272 by the receipt of the end signal by the three-dimensional display TV 10. If the end signal is not present in step S4070 (no in S4070), the processing returns to step S4010 and steps S4010 through S4020 are repeated until the receipt of the eyeglasses ID reception signal. If the end signal is present in step S4070 (yes in S4070), the processing proceeds to step S4090, and the operation of the three-dimensional eyeglasses 20 ends.

In step S4030, the transmission specification reception unit 272 checks if the three-dimensional eyeglasses 20 have received the eyeglasses specification request signal from the three-dimensional display TV 10 (communication 3, S4030). If the three-dimensional eyeglasses 20 have received the eyeglasses specification request signal in step S4030 (yes in S4030), the transmission specification reception unit 272 transmits the transmission specification of the three-dimensional eyeglasses 20 stored in the transmission specification store 260 (the communication 4, S4040). On the other hand, if the three-dimensional eyeglasses 20 do not receive the eyeglasses specification request signal in step S4030 (no in S4030), the processing proceeds to step S4050.

In step S4050, the signal generation controlling unit 252 checks if the transmission specification reception unit 272 has received a measurement abort signal (S4050). If the transmission specification reception unit 272 does not receive the measurement abort signal in step S4050 (no in S4050), the processing proceeds to step S5000. On the other hand, if the transmission specification reception unit 272 receives the measurement abort signal in step S4050 (yes in S4050), the signal generation controlling unit 252 stops the biometric signal sensor 240 and deletes the biometric signal data accumulated in the biometric signal store 251 (S4060). Subsequently, the signal generation controlling unit 252 checks if there is the end signal, that is, checks if either of the following is present: input has been made by the power switch (not shown); and the transmission specification reception unit 272 has received the end signal (S4080). If there is the end signal in step S4080 (yes in S4080), the processing proceeds to step S4090, and the operation of the three-dimensional eyeglasses 20 ends. On the other hand, if there is no end signal in step S4080 (no in S4080), step S4080 is repeated.

In step S5000, the signal generation controlling unit 252 checks if the transmission specification reception unit 272 has received a data transmission specification signal (a signal designating the transmission specification, i.e., the specification-designating signal) from the three-dimensional display TV 10 (S5000). If the transmission specification reception unit 272 has received the data transmission specification signal in step S5000 (the communication 5) (yes in S5000), the processing proceeds to step S5010. On the other hand, if the transmission specification reception unit 272 does not receive the data transmission specification signal in step S5000 (no in S5000), the processing returns to step S4030, and steps S4030 through S5000 are repeated to determine the data transmission specification.

In step S5010, the signal generation controlling unit 252 selects a process to be performed on the biometric signal by the biometric signal processing unit 253 and a specification of the transmission signal (i.e., the transmission specification) generated by the transmission signal generation unit 254, based on the data transmission specification signal (the specification-designating signal) received by the transmission specification reception unit 272, provided that step S5010 is executed only when the three-dimensional eyeglasses 20 have plural processing schemes for the biometric signal and can generate a transmission signal adapted to each processing scheme. When the three-dimensional eyeglasses 20 have one processing scheme for the biometric signal stored therein, step S5010 is not executed.

Subsequently, the signal generation controlling unit 252 checks if there is the end signal (S1040). When there is the end signal in step S1040 (yes in S1040), the processing proceeds to step S4090 and the operation of the three-dimensional eyeglasses 20 ends. On the other hand, if there is no end signal in step S1040 (no in S1040), the control signal reception unit 210 receives the shutter control signal (the communication 7, S5030), and, according to the control signal received in step S5030, the shutter control unit 220 switches the shielded state and the open state of the shutters (not shown) (S5040). This sets the right-eye shutter to the open state and the left-eye shutter to the shielded state in the three-dimensional eyeglasses 20 when the right-eye image is presented to the screen of the three-dimensional display TV 10. On the other hand, when the left-eye image is presented on the screen of the three-dimensional display TV 10, the left-eye shutter is set to the open state and the right-eye shutter is set to the shielded state in the three-dimensional eyeglasses 20. In other words, switching the shutters in synchronization with the screen display of the three-dimensional display TV 10 can correctly present the left and the right images to the viewer's left and right eyes, respectively, allowing the user to view the three-dimensional image.

Moreover, when there is no end signal in step S1040 (no in S1040), additionally, the biometric signal processing unit 253 checks if the biometric signals more than for a series of a predetermined signal processing are accumulated in the biometric signal store 251 (S5020) in parallel with the above processing (S5030 and S5040). If the biometric signals for the predetermined time duration are not accumulated in step S5020 (no in S5020), the processing returns to step S1040.

During repetition of step S1040 and step S5020, if the biometric signals for the predetermined time duration are accumulated in step S5020 in which the measurement and the accumulation of the biometric signals started in step S4000 are conducted (yes in S5020), the biometric signal processing unit 253 performs the signal processing determined in step S5010 and analyzes data. Subsequently, the transmission signal generation unit 254 converts the processing result or the analysis result into the transmission data in the specification determined in step S5010 (S1060). Details of the signal processing and generation of the transmission data will be described below.

After the execution of step S1060, the processing returns to step S1040. Then, steps S1040 through S1060 are repeated, continuously transmitting the biometric signals to the three-dimensional display TV at predetermined intervals until input of the end signal. This allows the image display system 100 to continuously monitor the viewer state as long as the viewer is viewing the three-dimensional image, enabling appropriate processing to the fatigue state of the viewer, as necessary.

<Description of Communication Data Format: Operation of Transmission Signal Generation Unit in Detail>

Figure 18:
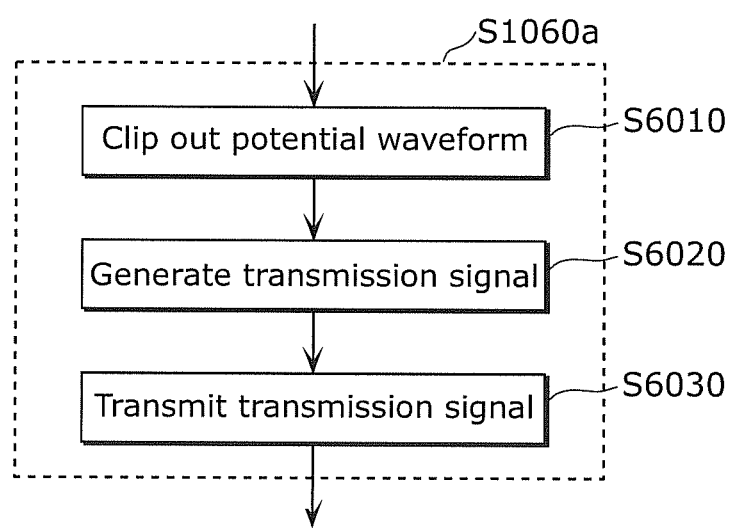
FIG. 18 is a flowchart illustrating an example of the detailed processing flow of a biometric signal data generation-transmission step according to the embodiment.
Figure 19:
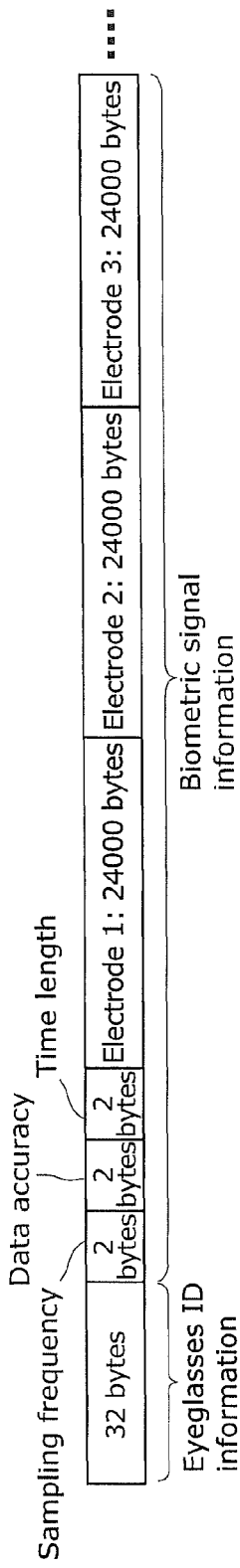
FIG. 19 is a diagram showing an example of a communication format in which a biometric signal is transmitted from the three-dimensional eyeglasses to the three-dimensional display TV according to the embodiment.

FIG. 17 is a block diagram of an example of the detailed configuration of the biometric signal processing unit 253 included in the three-dimensional eyeglasses 20 (herein, showing the configuration of the biometric signal processing unit 253*a*). The biometric signal processing unit 253*a* is a processing unit which performs the signal processing (i.e., the processing to generate the raw sensor output (raw data)) corresponding to the data level ID being 001, and includes a timer 711 and a signal processing unit 712. FIG. 18 is a flowchart illustrating an example of the process details of step S1060 of the processing performed by the three-dimensional eyeglasses 20 (herein, the processing of the biometric signal processing unit 253*a* (S1060*a*)). FIG. 19 is a diagram showing an example of the format of the transmission data generated by the biometric signal processing unit 253*a*, and, more particularly, (a) of FIG. 19 illustrates a case of transmission in binary data or text data, (b) of FIG. 19 illustrates a case of transmission of data described in an XML format. FIGS. 17, 18, and 19 are explanatory diagrams showing examples where the transmission specification is a transmission specification in which the potential is measured during each sampling period, using electrooculogram at the measurement electrodes and the reference electrode, and transmitted as 16 bits of a numerical sequence. The transmission specification is a data specification used in a case where, once the three-dimensional display TV 10 receives the biometric signal, steps S3021 through S3030 are executed by the convergence and divergence movements speed change processing unit 601 and the fatigue determination is conducted.

The timer 711 counts a predetermined time corresponding to one signal processing defined in specification. The signal processing unit 712 checks if the biometric signals for predetermined time duration are accumulated in the biometric signal store 251 (S5020). If the biometric signals for the predetermined time duration are not accumulated in step S5020 (no in S5020), the processing returns to step S1040. On the other hand, if the biometric signals for the predetermined time duration are accumulated in step S5020 (yes in S5020), the signal processing unit 712 clips and reads out the biometric signals for the predetermined time duration from the biometric signal store 251 (S6010).

Subsequently, assuming that the four measurement electrodes are the electrodes 1 to 4 and the reference electrode is the electrode 5, the transmission signal generation unit 254 uses the data read out in step S6010 to generate the transmission data in a transmission format sequentially describing numerical sequences of the potentials measured at the electrodes, starting from a numerical sequence of the potential at the electrode 1 for one minute, a numerical sequence of the potential at the electrode 2 for one minute, and so on, to a numerical sequence of the potential at the electrode 5 for one minute (S6020). Here, the transmission signal generation unit 254 describes the transmission data in binary data, text data, or an XML format as shown in FIG. 19 to generate the transmission signal.

Last, the eyeglasses information transmission unit 271 transmits the transmission signal generated by the transmission signal generation unit 254 in step S6020 to the three-dimensional display TV 10 (S6030).

Figure 20:
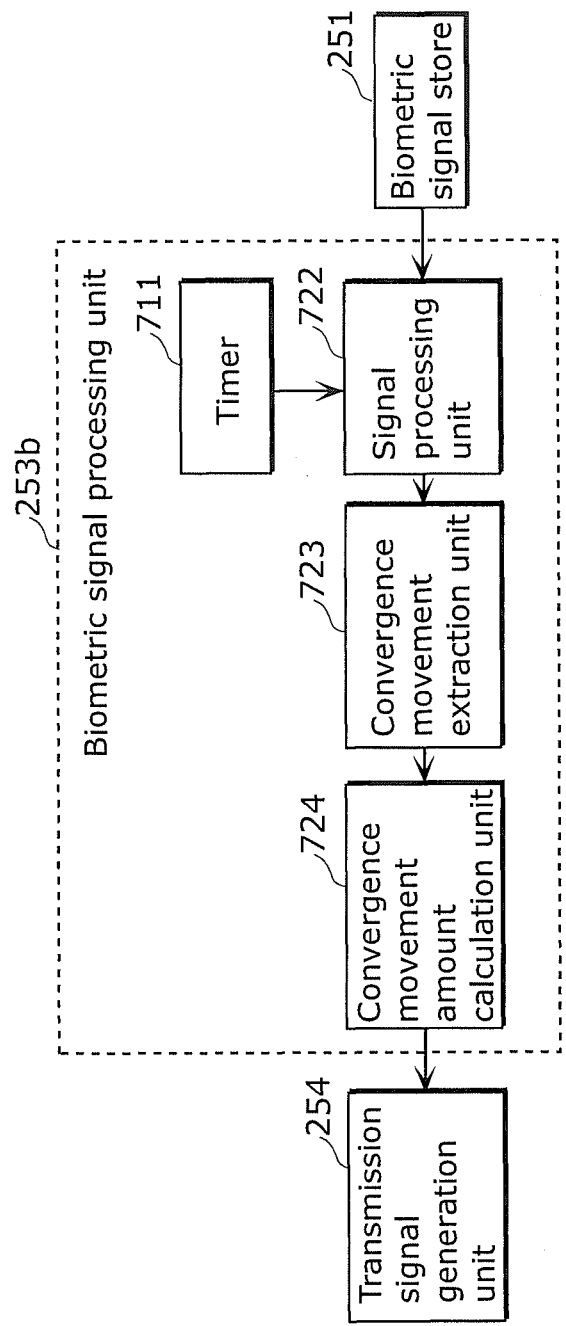
FIG. 20 is a block diagram showing an example of the detailed configuration of a biometric signal processing unit according to the embodiment.
Figure 21:
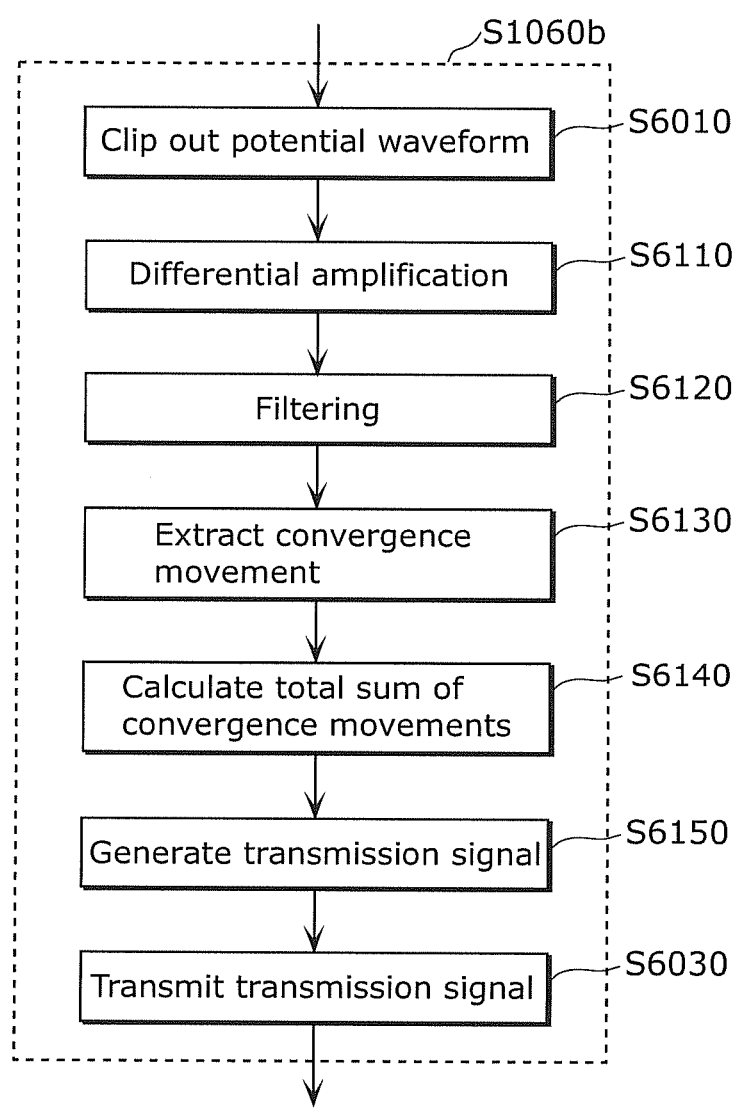
FIG. 21 is a flowchart illustrating an example of the detailed processing flow of a biometric signal data generation transmission step according to the embodiment.
Figure 22:
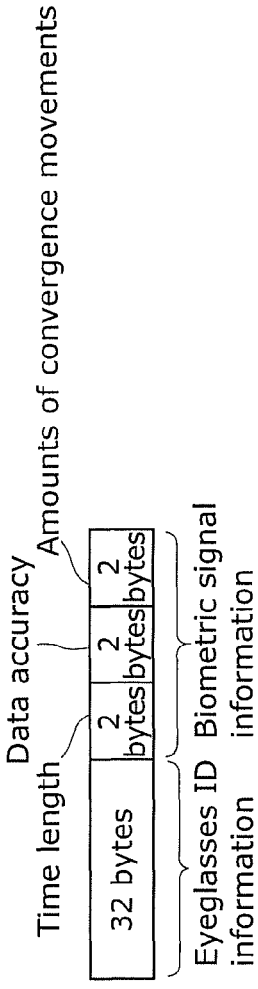
FIG. 22 is a diagram showing an example of a communication format in which a biometric signal is transmitted from the three-dimensional eyeglasses to the three-dimensional display TV according to the embodiment.

FIG. 20 is a block diagram of an example of the detailed configuration of the biometric signal processing unit 253 included in the three-dimensional eyeglasses 20 (herein, showing the configuration of the biometric signal processing unit 253*b*). The biometric signal processing unit 253*b* is a processing unit which performs the signal processing corresponding to the case where the data level ID is 002 (i.e., a process to generate data (the result of intermediate processing) that has undergone the signal processing such as filtering), and includes the timer 711, a signal processing unit 722, a convergence movement extraction unit 723, and a convergence movement amount calculation unit 724. FIG. 21 is a flowchart illustrating an example of the process of step S1060 of the processing performed by the three-dimensional eyeglasses 20 (herein, the processing of the biometric signal processing unit 253*b* (S1060*b*)). FIG. 22 is a diagram showing an example of the format of the transmission data generated by the biometric signal processing unit 253*b*, and, more particularly, (a) of FIG. 22 illustrates a case of transmission in binary data or text data, and (b) of FIG. 22 illustrates a case of transmission of data described in an XML format. The examples given in FIGS. 20, 21 and 22 are explanatory diagrams showing examples where the transmission specification is a specification in which the convergence and divergence movements are extracted from the electrooculogram and a grand total value of amounts of movements in the predetermined time period is transmitted as 16 bits of a numerical value. The transmission specification is a data specification used in a case where once the three-dimensional display TV 10 receives the biometric signal, the convergence and divergence movement amounts processing unit 602 conducts the fatigue determination through the processes of steps S3041 through S3043.

The timer 711 counts the predetermined time corresponding to the series of the signal processing determined in the specification. The signal processing unit 722 checks if the biometric signals for the predetermined time duration are accumulated in the biometric signal store 251 (S5020). If the biometric signals for the predetermined time duration are not accumulated in step S5020 (no in S5020), the processing returns to step S1040. On the other hand, if the biometric signals for the predetermined time duration are accumulated in step S5020 (yes in S5020), the signal processing unit 722 clips and reads out the biometric signals for the predetermined time duration from the biometric signal store 251 (S6010).

Subsequently, the signal processing unit 722 uses the data read out in step S6010 and performs differential amplification between each of the four measurement electrodes and the reference electrode (S6110). The differential amplification is performed by subtracting the potential of the reference electrode from the potential of the measurement electrode for each sample point of the potential. This can remove a wide range of noise common to the measurement electrodes and the reference electrode.

Then, the signal processing unit 722 passes the time waveforms of the potentials of the four differential amplified measurement electrodes through a band pass filter (S6120). The band pass filter is, for example, a filter having a passband of 10 Hz to 100 Hz. This can retrieve the range of relatively quick eye movements as the fatigue indicator and remove noise caused by muscles around the eyes or the like.

Subsequently, the convergence movement extraction unit 723 takes the difference between the potential waveforms of the four measurement electrodes, which have been filtered in step S6120, to remove the horizontal component and the vertical component common to both eyes (S6130). Specifically, if the electrodes are disposed as illustrated in FIG. 6 for example, the convergence movement extraction unit 723 calculates, as the component of the movement common to both eyes and in the horizontal direction, a difference between the differential amplified potential waveforms of the measurement electrode 1 and the differential amplified potential waveforms of the measurement electrode 4 which are disposed in parallel to the horizontal axis of the viewer's face. Moreover, as a component of the movement common to both eyes and in the vertical direction, the convergence movement extraction unit 723 calculates a difference between the mean of the differential amplified potentials at the measurement electrodes 1 and 4 located at common positions on the vertical axis of the viewer's face and the mean of the differential amplified potentials at the measurement electrodes 2 and 3. Furthermore, the convergence movement extraction unit 723 obtains a difference between the differential amplified potential waveforms at the measurement electrodes 1 and 2 as the right-eye movement potential, and obtains a difference between the differential amplified potential waveforms at the measurement electrodes 4 and 3 as the left-eye movement potential. Last, the convergence movement extraction unit 723 subtracts the previously obtained components of movements common to both eyes and in the horizontal and vertical directions from the eye movement potential of both eyes to extract the component of the convergence movement of the viewer's right eye and the component of the convergence movement of the viewer's left eye.

Next, the convergence movement amount calculation unit 724 obtains a potential difference between a peak and the following peak for all peaks of the potential fluctuations of the component waveforms of each of the left and right eye convergence movements obtained in step S6130 and obtains a total sum of absolute values of the obtained potential differences to calculate the amount of convergence movement (S6140).

Then, the transmission signal generation unit 254 describes the transmission data in binary data, text data, or an XML format as shown in FIG. 22 to generate the transmission signal (S6150).

Last, the eyeglasses information transmission unit 271 transmits the transmission signal generated by the transmission signal generation unit 254 in step S6150 to the three-dimensional display TV 10 (S6030).

In such a manner, by the three-dimensional eyeglasses 20 transmitting to the three-dimensional display TV 10 the result of intermediate processing as a process of conversion from the biometric signal to the fatigue indicator, a large amount of data to communicate can be reduced.

In the above example, the sum of the convergence movements is outputted as the intermediate output. However, an average speed of the convergence movement, average saccadic velocity, or the result of intermediate processing such as saccade and blink rate may be outputted. As the example given in FIG. 5, depending on the content of the biometric information utilized for the calculation of the fatigue indicator, computational load and the amount of data at the measurement of the biometric signal or through the signal processing vary. The method of outputting the result of intermediate processing allows for the adjustment (balancing) between the three-dimensional eyeglasses 20 and the three-dimensional display TV 10 with respect to the computation, memory burden and the communication load. Thus, a specification that meets manufacturing cost or power consumption can be set.

Figure 23:
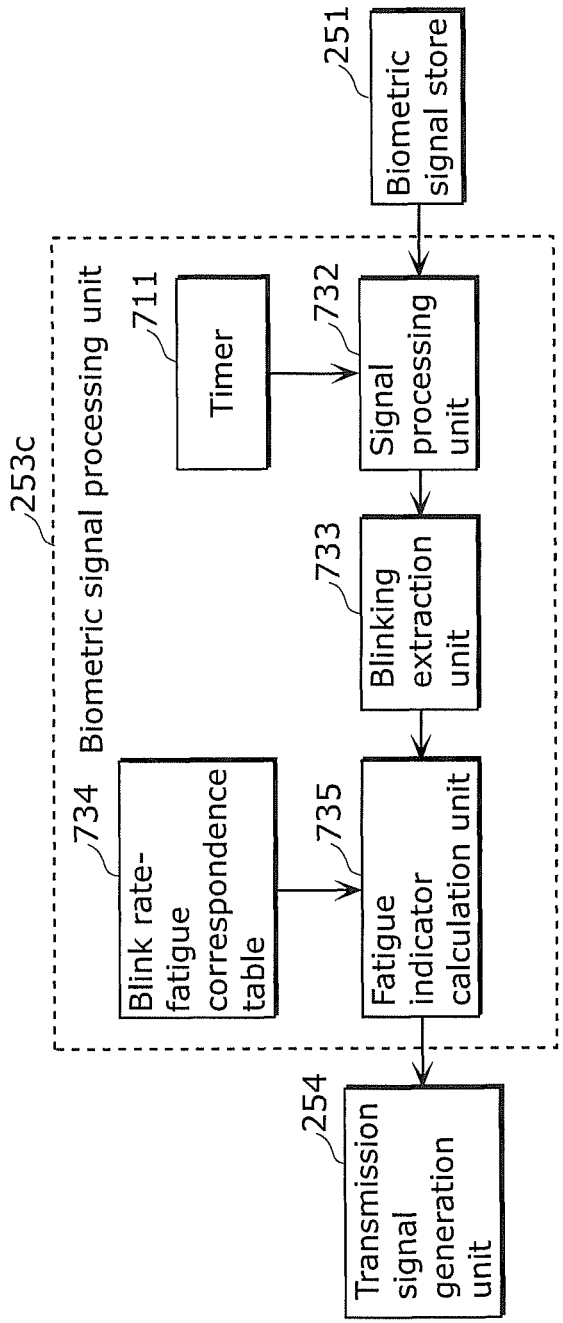
FIG. 23 is a block diagram showing an example of the detailed configuration of a biometric signal processing unit according to the embodiment.
Figure 24:
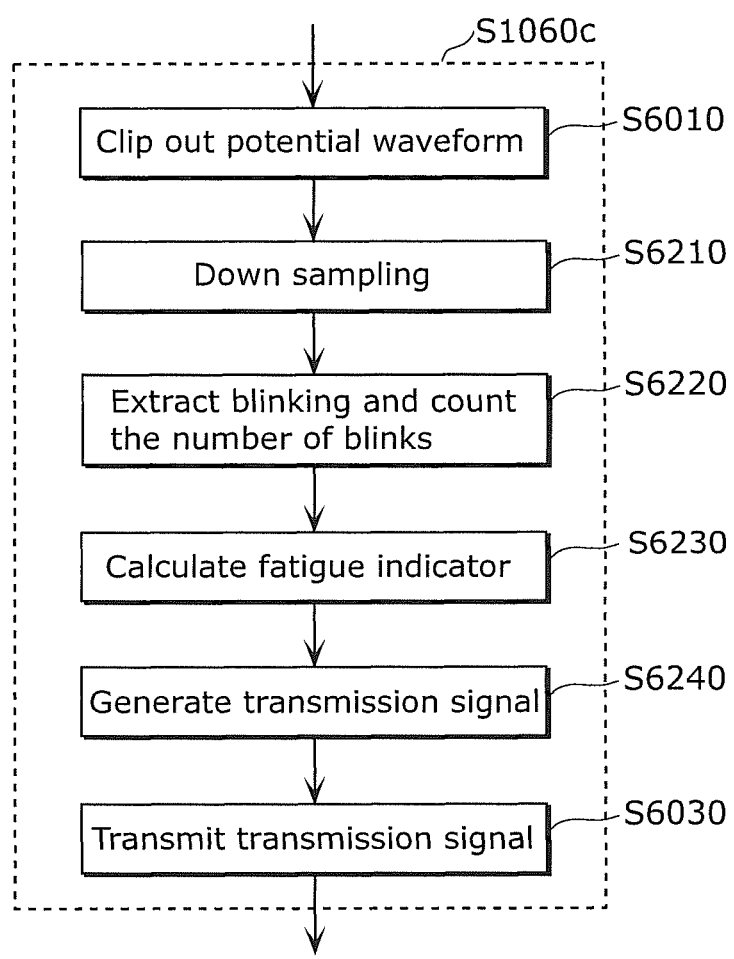
FIG. 24 is a flowchart illustrating an example of the detailed processing flow of a biometric signal data generation·transmission step according to the embodiment.
Figure 26:
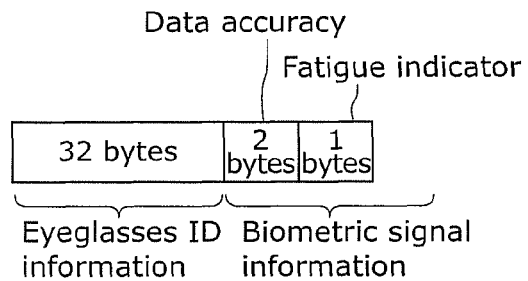
FIG. 26 is a diagram showing an example of a communication format in which a biometric signal is transmitted from the three-dimensional eyeglasses to the three-dimensional display TV according to the embodiment.

FIG. 23 is a block diagram of an example of the detailed configuration of the biometric signal processing unit 253 included in the three-dimensional eyeglasses 20 (herein, showing the configuration of the biometric signal processing unit 253c). The biometric signal processing unit 253c is a processing unit which performs signal processing corresponding to the case where the data level ID is 003 (i.e., processing to generate data indicative of the result of determining the viewer state (for example, the level of fatigue)), and includes the timer 711, a signal processing unit 732, a blinking extraction unit 733, a blink rate-fatigue correspondence table 734, and a fatigue indicator calculation unit 735. FIG. 24 is a flowchart illustrating an example of the process details of step S1060 of the processing performed by the three-dimensional eyeglasses 20 (herein, the processing of the biometric signal processing unit 253c (S1060c)). FIG. 26 is a diagram showing an example of the format of the transmission data generated by the biometric signal processing unit 253c, and, more specifically, (a) of FIG. 26 shows the case of transmission in binary data or text data, and (b) of FIG. 26 illustrates a case of transmission of data described in an XML format. FIGS. 23, 24, and 26 are explanatory diagrams showing examples where the transmission specification is a specification in which blinking is extracted from electrooculogram, and the fatigue indicator is obtained based on the number of blinks in the predetermined time period and transmitted as 8 bits of a numerical value. The transmission specification is a data specification used in a case where, once the three-dimensional display TV 10 receives the biometric signal, the fatigue indicator acquisition unit 603 conducts the fatigue determination through the process of step S3051.

The timer 711 counts a predetermined time corresponding to a series of the signal processing. The signal processing unit 732 checks if the biometric signals for predetermined time duration are accumulated in the biometric signal store 251 (S5020). If the biometric signals for the predetermined time duration are not accumulated in step S5020 (no in S5020), the processing returns to step S1040. On the other hand, if the biometric signals for the predetermined time duration are accumulated in step S5020 (yes in S5020), the signal processing unit 732 clips and reads out the biometric signals for the predetermined time duration from the biometric signal store 251 (S6010).

Subsequently, the signal processing unit 732 down samples the data read out in step S6010 to a sampling frequency of 50 Hz (S6210).

Then, the blinking extraction unit 733 extracts the blinking and counts the number of the blinks (S6220). Specifically, if the electrodes are arranged as shown in FIG. 6, for example, the blinking extraction unit 733 subtracts the potential waveforms of the electrode 2 from the potential waveforms of the electrode 1 to obtain potential fluctuations of the right eye. Meanwhile, the blinking extraction unit 733 subtracts the potential waveforms of the electrode 3 from the potential waveforms of the electrode 4 to obtain potential fluctuations of the left eye. The blinking extraction unit 733 then obtains a sum of the potential fluctuations of the right and the left eyes to obtain a potential difference between a peak and the following peak for all peaks of the potential fluctuations. Furthermore, the blinking extraction unit 733 extracts, as blinking, the potential difference between peaks that is greater than or equal to a predetermined threshold value, for example, greater than or equal to 200 µV, and counts the number of blinks per predetermined time period, for example, per ten minutes.

Next, the fatigue indicator calculation unit 735 specifies the fatigue indicator corresponding to the counted number of blinks per unit time, based on the correspondence between the number of blinks per unit time and a fatigue indicator stored in the blink rate-fatigue correspondence table 734, thereby obtaining the fatigue indicator (S6230). An example of the correspondence between the number of blinks ("Blink rate (count)") and the "Fatigue indicator" stored in the blink rate-fatigue correspondence table 734 is shown in FIG. 25. In general, the number of blinks decreases as the eyes are getting fatigued. Thus, values in the table are set so that lower blink rate increases the fatigue indicator.

The transmission signal generation unit 254 describes the transmission data in binary data, text data, or an XML format as shown in FIG. 26 to generate the transmission signal (S6240).

Last, the eyeglasses information transmission unit 271 transmits the transmission signal generated by the transmission signal generation unit 254 in step S6240 to the three-dimensional display TV 10 (S6030).

The blinking is easier to measure than electrooculogram. Thus, electrooculogram can be used to measure the blinking even if the accuracy of the biometric sensor is poor, acquiring the biometric signal at low cost.

While the fatigue indicator is calculated using the blink rate and transmitted to the three-dimensional display TV 10 in the above example, the fatigue indicator obtained using other biometric information as shown in FIG. 5 may be transmitted.

Moreover, in the above example, FIGS. 17, 20, and 23 have been described as the example of the detailed configurations of the biometric signal processing unit 253 in FIG. 14. However, the biometric signal processing unit 253 may include any one of the configurations shown in FIGS. 17, 20 and 23, or may include multiple (for example, all) of the configurations. When the biometric signal processing unit 253 includes the configurations shown in FIGS. 17, 20, and 23 (i.e., a plurality of configurations), the biometric signal processing unit 253 selects a configuration for operation, from among the multiple configurations, in step S5010, according to the transmission specification received in step S5000. This allows for the optimization of the complexity, the amount of data, and the communication traffic between the three-dimensional display TV 10 and the three-dimensional eyeglasses 20.

In the present embodiment, the following three cases have been described: (1) the electrooculogram at each electrode is transmitted from the three-dimensional eyeglasses 20, the three-dimensional display TV 10 receives the electrooculogram, and calculates the fatigue indicator, utilizing the change in speed of the convergence and divergence movements; (2) the total sum, per unit time, of the amounts of convergence and divergence movements is transmitted from the three-dimensional eyeglasses 20, the three-dimensional display TV 10 receives the total sum of the amounts of convergence and divergence movements and converts the total sum of the amounts of convergence and divergence movements into the fatigue indicator; (3) by the three-dimensional eyeglasses 20 utilizing the electrooculogram at the electrodes and calculating the total sum of the amounts of convergence and divergence movements, the fatigue indicator is transmitted from the three-dimensional eyeglasses 20, the three-dimensional display TV 10 receives the fatigue indicator and performs only the fatigue determination, i.e., the electrooculogram at each electrode is utilized to extract the blinking and the fatigue indicator is calculated in the three-dimensional eyeglasses 20. However, there are various methods for obtaining the fatigue indicator from the electrooculogram as illustrated in FIG. 5.

In any method for using the electrooculogram to obtain the fatigue indicator, the potential data is filtered and the signal processing is performed such as calculating the difference of potential waveforms between the electrodes, and the intermediate output which is the result of the signal processing is obtained. Infinite patterns of the data transmission specification of the biometric signal are conceivable depending on (1) the biometric signal employed (such as convergence and divergence movements, involuntary eye movement, saccade, and blinking) and (2) whether output from the biometric signal sensor 240 is transmitted as outputted and all the processing is performed by the three-dimensional display TV 10, whether the output of the intermediate processing is transmitted and the processing from the intermediate processing output to the fatigue indicator calculation is performed by the three-dimensional display TV 10, or whether up to the fatigue indicator calculation is performed by the three-dimensional eyeglasses 20 and the three-dimensional display TV 10 performs only the fatigue determination, i.e., determines the presentation to the viewer.

Furthermore, if the signal processing includes multiple phases, the intermediate output exists at each phase. The configuration of the viewer state calculation unit 162 may be achieved in software, and if the transmission specification of the transmission data of the biometric signal transmitted from the three-dimensional eyeglasses 20 cannot be utilized by the three-dimensional display TV 10 in step S1020, the biometric signal having the transmission specification of the three-dimensional eyeglasses 20 may be utilized by acquiring software supporting the transmission specification transmitted from the three-dimensional eyeglasses 20 via a network or by acquiring the software from a medium such as a DVD distributed with the eyeglasses.

In the present embodiment, the example has been given where the potentials, of biometric signals, varying according to the eye movements are measured, using the electrodes mounted on the three-dimensional eyeglasses 20 around the eyes and the viewer fatigue is determined. In addition to this, the eye movements and the viewing directions, the responses of the pupils, blinking, and the like which are calculated from the eye movements may be acquired as the biometric signal from an eye image, and the fatigue, the level of alertness, or the degree of excitement of the viewer may be determined. Moreover, the degree of excitement or the level of alertness of the viewer may be determined from change in electrical resistance of the skin owning to emotional sweating obtained by an electrode in contact with the forehead. Moreover, a light source and a camera may be provided pinching the nose, and vein patterns may be imaged using transmission of near infrared light for the personal identification to limit viewable content items or adapt the level of depth to the individual.

As described above, the present disclosure relates to a technology in which the biometric signal which includes the eye state is measured by the three-dimensional eyeglasses to determine the viewer state, and, based on the measurement result, the video display of the three-dimensional display TV is controlled. In general, there is a specific analysis method for the biometric signal, according to the type of the signal. Thus, the present disclosure is achieved to overcome a problem that the viewer state cannot be determined, despite the biometric signal is sensed by the three-dimensional eyeglasses 20, when there is no correspondence between the biometric signal analysis method executable by the three-dimensional display TV 10 and the biometric signal sensed by the three-dimensional eyeglasses 20.

For example, the potential data (corresponding to the data where "Data level ID" is 001 in FIG. 4) for each electrode, measured by the electrodes for measuring the electrooculogram which are mounted on the three-dimensional eyeglasses 20 is filtered (S3023). Furthermore, using the potential differences between the measurement electrodes at sample points, the components (corresponding to data where "Data level ID" is 002 in FIG. 4) of the convergence movement which is included in the measured electrooculogram are extracted (S3024). The fatigue indicator (corresponding to data where "Data level ID" is 003 in FIG. 4) is obtained from the change in speed of the component of the convergence movement (S3025 through S3030). Here, the three-dimensional eyeglasses 20 may transmit the potential data at each electrode and the three-dimensional display TV 10 may receive the component data of the convergence movement. In this case, the data levels of the three-dimensional eyeglasses 20 and the three-dimensional display TV 10 do not match and the three-dimensional display TV 10 fails to process the received data.

To solve the above problem, the present embodiment matches the transmission specification in which the data level at which the three-dimensional eyeglasses 20 can output the biometric signal is clarified and the reception specification in which the data level at which the three-dimensional display TV 10 can receive and utilize the biometric signal is clarified. In order to do this, the three-dimensional eyeglasses 20 include the transmission specification store 260, while the three-dimensional display TV 10 includes the measurement specification store 163, the measurement specification determination unit 161, and the transmission specification transmission unit 152.

Then, to determine the data level at which the data is to be transmitted from the three-dimensional eyeglasses 20 to the three-dimensional display TV 10, the three-dimensional eyeglasses 20 transmit, over the communication 4 in FIG. 2, to the three-dimensional display TV 10 the transmission specifications, stored in the transmission specification store 260, that includes the information on the data level at which the three-dimensional eyeglasses 20 can transmit the data. The three-dimensional display TV 10 receives the transmission specification transmitted from the three-dimensional eyeglasses 20 (S2030), the measurement specification determination unit 161 refers to the measurement specification store 163 and selects one transmission specification corresponding to the measurement specification that matches the transmission specification transmitted from the three-dimensional eyeglasses 20 (S2040 through S2060), and transmits the just selected transmission specification (i.e., the specification-designating signal) to the three-dimensional eyeglasses 20 over the communication 5 (S2070). The three-dimensional eyeglasses receive the transmission specification that is transmitted in step S2070 (S5000), and according to the transmission specification, determines a data specification, which includes the data level, to be transmitted by the three-dimensional eyeglasses 20 (S5010).

Thus in the embodiment, the configurations and the operations for matching the data specifications including the data levels at which the three-dimensional display TV 10 receives the biometric signal and the three-dimensional eyeglasses 20 transmit the biometric signal can alleviate the viewer fatigue by adjusting the video displayed on the three-dimensional display TV 10, using the biometric signals acquired by the three-dimensional eyeglasses 20, irrespective of the combination of the three-dimensional display TV 10 and the three-dimensional eyeglasses 20.

Japanese Unexamined Patent Application Publication No. 2011-188118 (PTL 3) discloses communication means from the three-dimensional eyeglasses to the image display apparatus, communicating the biometric signal from the three-dimensional eyeglasses to the image display apparatus, and communicating a signal identifying the attributes of the three-dimensional eyeglasses from the three-dimensional eyeglasses to the image display apparatus. However, PTL 3 fails to disclose communicating the data specification (i.e., the transmission specification) specifying the processing state (i.e., data level) of the biometric signal.

As described above, according to the present embodiment, the biometric signals of the viewer during viewing the three-dimensional image are acquired and the biometric information is transmitted from the three-dimensional eyeglasses to the image display apparatus at the data level of any of: raw signal; the result of intermediate processing; and the result of processing. This allows for the determination of the viewer state in the image display apparatus and the image display method or the like to be changed for the viewer state. The three-dimensional image viewing with comfort is achieved which, for example, presents the viewer with the fatigue state alert for signs of fatigue even the viewer is unaware of.

As set forth above, the image display system and the three-dimensional eyeglasses have been described with reference to a certain embodiment. However, the present disclosure is not limited to the embodiment. Various modifications to the present embodiment that may be conceived by those skilled in the art and a form obtained by any combination of the present embodiment and well-known components are included in the present disclosure, without departing from the spirit of the present disclosure.

Moreover, each of the functional blocks shown in the block diagrams (FIG. 1, FIG. 7, FIG. 8, FIG. 14, FIG. 17, FIG. 20, FIG. 23) of the present embodiment may be achieved in the form of an integrated circuit or an LSI. The LSI may be mounted on one chip for each functional block, or some or all the functional blocks may be mounted on one chip in the three-dimensional display TV 10 and the three-dimensional eyeglasses 20. Here, the term LSI is used. However, IC, system LSI, super LSI, ultra LSI may be used depending on the difference in degree of integration.

Moreover, ways to achieve integration are not limited to the LSI, and a special circuit or a general purpose processor and so forth can also achieve the integration. An FPGA (Field Programmable Gate Array) which is programmable after manufacturing the LSI, or a reconfigurable processor in which connection or settings of circuit cells in LSI is reconfigurable, may be utilized for the integration.

Figure 27:
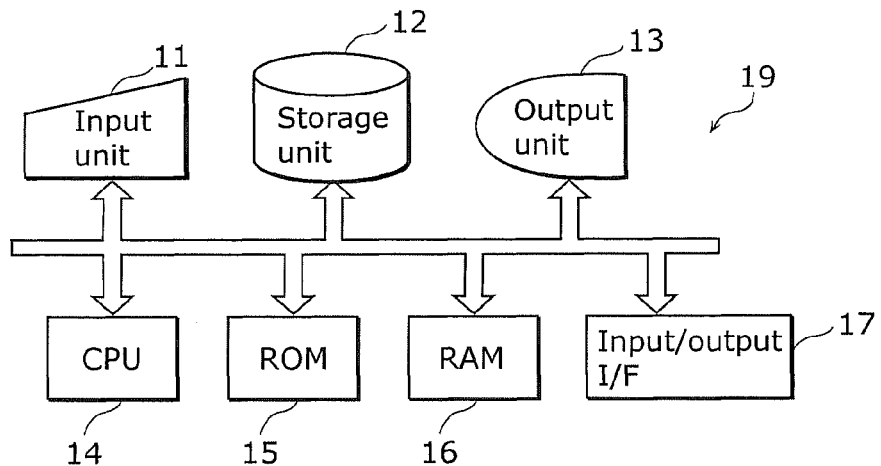
FIG. 27 is a block diagram of a hardware configuration used for implementing the three-dimensional display TV according to the embodiment in a computer system and software.

Moreover, the image display apparatus (the three-dimensional display TV according to the present embodiment or the like) included in the image display system may be implemented in a computer system or software. FIG. 27 is a block diagram of a hardware configuration used for implementing the three-dimensional display TV 10 according to the present embodiment in a computer system 19 and software. The computer system 19 includes, as shown in FIG. 27, an input unit 11 such as a keyboard and a mouse, a storage unit 12 such as a hard disk, an output unit 13 such as a display device, a CPU 14, a ROM 15, a RAM 16, and an input/output I/F 17 which inputs/outputs signals to/from an external device. Specifically, the transmitting and receiving unit 150, and the control signal transmission unit 130 are each implemented in the input/output I/F 17. The information presentation unit 170 is implemented in the output unit 13. The content information store 110 is implemented in the storage unit 12. The screen control unit 120, the communication control unit 140, and the viewer state determination unit 160 are each implemented by the CPU 14 utilizing the RAM 16 as a temporary storage area and executing a program stored in the ROM 15 or the storage unit 12. Herein, the computer program includes a combination of a plurality of instruction codes indicative of instructions to the computer to achieve predetermined functionality.

Moreover, some or all components included in the three-dimensional display TV according to the above embodiment may be configured with a detachable IC card or a detachable single module. The IC card or the module is a computer system which includes a microprocessor, a ROM, a RAM, or the like. The IC card or the module may include a super multi-function LSI. The IC card or the module performs its functionality by the microprocessor operating according to the computer program. The IC card or the module may be of tamper-resistant.

Moreover, the present disclosure may be achieved as the method (the image display method by the image display system) illustrated in the flowcharts provided in the above embodiment. Moreover, the present disclosure may be implemented as a computer program for causing a computer to execute the method or a digital signal representing the computer program. Furthermore, the computer or the digital signal may be implemented in a computer-readable recording medium having the computer or the digital signal recorded therein, such as a flexible disk, a hard disk, a CD-ROM, a MO, a DVD, a DVD-ROM, a DVD-RAM, a BD (Blu-ray Disc (registered trademark)), and a semiconductor memory.

Moreover, the computer program or the digital signals may, of course, be transmitted via an electric communication line, a wireless or wired communication line, a network represented by the Internet, data broadcast, or the like.

Moreover, by transferring the program or the digital signals recorded in the non-transitory recording medium, or transferring the program or the digital signals via the network or the like, the image display apparatus or the method in the image display system may be performed in other independent computer system.

The herein disclosed subject matter is to be considered descriptive and illustrative only, and the appended Claims are of a scope intended to cover and encompass not only the particular embodiments) disclosed, but also equivalent structures, methods, and/or uses.

INDUSTRIAL APPLICABILITY

An image display system according to one or more exemplary embodiments disclosed herein are widely applicable to an image display system in which a stereoscopic video is viewed using three-dimensional eyeglasses, and are useful for displaying three-dimensional videos on movie screens, TVs, and computer display screens. Thus, the present disclosure is applicable not only to content viewing but also to image display on medical equipment such as diagnostic imaging devices and endoscopes, games such as simulated surgery and simulated vehicle ride, and training systems.

The invention claimed is:

1. An image display system for presenting a three-dimensional image to a viewer, the image display system comprising:
    an image display apparatus for alternately outputting a left-eye image and a right-eye image to be presented to a left eye and a right eye, respectively, of a viewer; and
    three-dimensional eyeglasses having a left-eye shutter and a right-eye shutter for being worn by the viewer over face or head and setting the left-eye shutter to an open state when the left-eye image is displayed by the image display apparatus and setting the right-eye shutter to the open state when the right-eye image is displayed by the image display apparatus,
    wherein the three-dimensional eyeglasses include:
        a biometric signal measurement unit configured to measure a physical state of the viewer and acquire a biometric signal; and
        a transmitting and receiving unit configured to convert the biometric signal acquired by the biometric signal measurement unit into a communication signal and transmit the communication signal to the image display apparatus,
    wherein the image display apparatus includes
        a transmitting and receiving unit configured to receive the communication signal transmitted from the three-dimensional eyeglasses,
    wherein the transmitting and receiving unit included in the image display apparatus is configured to transmit, to the three-dimensional eyeglasses, a specification-designating signal designating a specification including a data format of the biometric signal for the communication signal, and
    wherein the transmitting and receiving unit included in the three-dimensional eyeglasses is configured to (i) receive the specification-designating signal transmitted from the image display apparatus, (ii) convert the biometric signal acquired by the biometric signal measurement unit into the communication signal according to the specification including the data format of the biometric signal designated by the received specification-designating signal, and (iii) transmit, to the image display apparatus, the communication signal according to the specification including the data format of the biometric signal.

2. The image display system according to claim 1,
    wherein the three-dimensional eyeglasses further include a transmission specification store storing at least one transmission specification which is information indicative of a specification in which the three-dimensional eyeglasses can transmit the communication signal to the image display apparatus,
    the transmitting and receiving unit included in the three-dimensional eyeglasses is further configured to transmit the at least one transmission specification stored in the transmission specification store to the image display apparatus, and the transmitting and receiving unit included in the image display apparatus is configured to receive the at least one transmission specification transmitted from the three-dimensional eyeglasses, and transmit to the three-dimensional eyeglasses, as the specification-designating signal, a signal indicative of at least one transmission specification selected from among the received at least one transmission specification.

3. The image display system according to claim 2, wherein the image display apparatus further includes:
  a measurement specification store storing at least one measurement specification which is information indicative of a specification in which the transmitting and receiving unit included in the image display apparatus can receive the communication signal; and
  a measurement specification determination unit configured to determine a measurement specification for use in determining the physical state of the viewer, from among the at least one measurement specification stored in the measurement specification store,
wherein the transmitting and receiving unit included in the image display apparatus is configured to transmit to the three-dimensional eyeglasses, as the specification-designating signal, a signal indicative of a transmission specification corresponding to the measurement specification determined by the measurement specification determination unit, among the at least one transmission specification transmitted from the three-dimensional eyeglasses.

4. The image display system according to claim 3, wherein the transmitting and receiving unit included in the three-dimensional eyeglasses is further configured to transmit an eyeglasses ID, which is a signal identifying the three-dimensional eyeglasses, to the image display apparatus,
the transmitting and receiving unit included in the image display apparatus is configured to receive the eyeglasses ID transmitted from the three-dimensional eyeglasses, and
the measurement specification determination unit is configured to determine whether a measurement specification corresponding to the received eyeglasses ID is stored in the measurement specification store and, determine the measurement specification as the one measurement specification when the measurement specification is stored in the measurement specification store, and request the three-dimensional eyeglasses to transmit a transmission specification stored in the transmission specification store to the image display apparatus when the measurement specification is not stored in the measurement specification store.

5. The image display system according to claim 2, wherein the transmission specification or the specification-designating signal includes an array of plural signals indicative of the physical state of the viewer measured by the biometric signal measurement unit and information describing an amount of data of each of the plural signals.

6. The image display system according to claim 1, wherein the biometric signal measurement unit is configured to measure electrooculogram of the viewer as the physical state of the viewer.

7. The image display system according to claim 1, wherein the biometric signal measurement unit is configured to measure galvanic skin response or skin potential of the viewer as the physical state of the viewer.

8. The image display system according to claim 1, wherein the biometric signal measurement unit is configured to image a portion of a body of the viewer as the physical state of the viewer.

9. The image display system according to claim 8, wherein the biometric signal measurement unit is configured to image a vein pattern of the viewer as the physical state of the viewer.

10. The image display system according to claim 1, wherein the biometric signal measurement unit is configured to acquire a time series signal indicative of the physical state of the viewer as the biometric signal.

11. The image display system according to claim 10, wherein the three-dimensional eyeglasses further include a biometric signal processing unit configured to perform signal processing for generating the time series signal acquired by the biometric signal measurement unit as a numerical sequence,
the transmitting and receiving unit included in the three-dimensional eyeglasses is configured to transmit the numerical sequence acquired by the biometric signal processing unit to the image display apparatus, and
the image display apparatus further includes a viewer state determination unit configured to determine the physical state of the viewer, based on the numerical sequence transmitted from the three-dimensional eyeglasses.

12. The image display system according to claim 11, wherein the specification-designating signal includes information specifying a data level indicative of a degree at which data included in the communication signal is to be processed, and
the biometric signal processing unit is configured to perform the signal processing, according to the data level specified by information included in the specification-designating signal transmitted from the image display apparatus.

13. The image display system according to claim 10, wherein the three-dimensional eyeglasses further include a biometric signal processing unit configured to perform signal processing on the time series signal acquired by the biometric signal measurement unit to generate a numerical value or a numerical sequence related to a body movement of the viewer,
the transmitting and receiving unit included in the three-dimensional eyeglasses is configured to transmit the numerical value or the numerical sequence acquired by the biometric signal processing unit to the image display apparatus, and
the image display apparatus further includes a viewer state determination unit configured to determine the physical state of the viewer, based on the numerical value or the numerical sequence transmitted from the three-dimensional eyeglasses.

14. The image display system according to claim 10, wherein the three-dimensional eyeglasses further include a biometric signal processing unit configured to perform signal processing on the time series signal acquired by the biometric signal measurement unit to generate a numerical value or a numerical sequence related to a body movement of the viewer, and determine the physical state of the viewer using the generated numerical value or the generated numerical sequence, and the transmitting and receiving unit included in the three-dimensional eyeglasses is configured to transmit a result of determining the physical state of the viewer by the biometric signal processing unit to the image display apparatus.

15. The image display system according to claim 1, wherein the physical state of the viewer represents a fatigue state of the viewer.

16. The image display system according to claim 1, wherein the physical state of the viewer represents individual identification of the viewer.

17. The image display system according to claim 1, wherein the transmitting and receiving unit included in the image display apparatus is configured to transmit, as the data format, the specification-designating signal designating the specification including a data format including at least one of a type, a number, a length, and an order of information included in the communication signal, to the three-dimensional eyeglasses.

18. Three-dimensional eyeglasses for being worn by a viewer over face or head and operating in cooperation with an image display apparatus, the three-dimensional eyeglasses comprising:
- a right-eye shutter and a left-eye shutter, states of which are switchable between an open state and a closed state;
- a biometric signal measurement unit configured to measure a physical state of the viewer and acquire a biometric signal; and
- a transmitting and receiving unit configured to convert the biometric signal acquired by the biometric signal measurement unit into a communication signal and transmit the communication signal to the image display apparatus,
- wherein the transmitting and receiving unit is configured to receive (i) a specification-designating signal designating a specification including a data format of the biometric signal for the communication signal, the specification-designating signal being transmitted from the image display apparatus, (ii) convert the biometric signal acquired by the biometric signal measurement unit into the communication signal according to the specification including the data format of the biometric signal designated by the received specification-designating signal, and (iii) transmit, to the image display apparatus, the communication signal according to the specification including the data format of the biometric signal.

19. The three-dimensional eyeglasses according to claim 18, further comprising
- a transmission specification store storing at least one transmission specification which is information indicative of a specification in which the three-dimensional eyeglasses can transmit the communication signal to the image display apparatus, wherein
- the transmitting and receiving unit is further configured to transmit the at least one transmission specification stored in the transmission specification store to the image display apparatus, and
- the image display apparatus receives the at least one transmission specification transmitted from the three-dimensional eyeglasses, and transmits, as the specification-designating signal, a signal indicative of at least one transmission specification selected from among the received at least one transmission specification to the three-dimensional eyeglasses.

20. The three-dimensional eyeglasses according to claim 19, wherein each of the at least one transmission specification stored in the transmission specification store includes:
- any of: information specifying a type of the biometric signal; information specifying a level at which the biometric signal is to be processed before the three-dimensional eyeglasses transmits information to the image display apparatus; frequency of the three-dimensional eyeglasses transmitting information to the image display apparatus; a sampling frequency and an amount of data of the sampling frequency upon acquisition of the biometric signal; data accuracy and an amount of data describing the data accuracy; a time length of the biometric signal and an amount of data of the time length; and a number of an electrode to be used for processing the biometric signal and an amount of data for describing the number of the electrode; and
- any of: an amount of data of the biometric signal for each electrode at which the biometric signal is measured; and a type of a result of intermediate processing and an amount of data describing the result of the intermediate processing; and a type of a result of determining the physical state of the viewer and an amount of data describing the physical state.

* * * * *